United States Patent [19]

Phillips et al.

[11] Patent Number: 5,437,287
[45] Date of Patent: Aug. 1, 1995

[54] STERILIZATION OF TISSUE IMPLANTS USING IODINE

[75] Inventors: Richard E. Phillips, San Marcos; Mark A. Moore, Austin, both of Tex.; Ruth L. Russell, Long Beach; David Cheung, Arcadia, both of Calif.

[73] Assignee: Carbomedics, Inc., Austin, Tex.

[21] Appl. No.: 931,280

[22] Filed: Aug. 17, 1992

[51] Int. Cl.[6] .................. A61B 19/00; A61F 2/06; A61F 2/02; A61F 2/54
[52] U.S. Cl. .................. 128/898; 128/897; 623/1; 623/11; 623/66; 424/667; 422/28; 422/37
[58] Field of Search .............. 623/1, 11, 66; 128/897, 128/898; 424/667; 422/37, 40, 28

[56] References Cited

U.S. PATENT DOCUMENTS

| | | | |
|---|---|---|---|
| Re. 31,035 | 9/1982 | Hancock et al. | 623/2 |
| 887,130 | 5/1908 | Schmidt . | |
| 1,006,854 | 10/1911 | Kuhn | 8/94.11 |
| 1,892,410 | 12/1932 | Rohm et al. . | |
| 3,152,976 | 10/1964 | Kuntz . | |
| 3,911,107 | 10/1975 | Krezanoski | 424/78 |
| 4,083,066 | 4/1978 | Schmitz et al. | 3/1.4 |
| 4,097,234 | 6/1978 | Sohde et al. | 8/94.19 |
| 4,120,649 | 10/1978 | Schechter | 8/94.11 |
| 4,278,548 | 6/1981 | Bettinger et al. | 210/636 |
| 4,314,800 | 2/1982 | Monsheimer et al. | 8/94.11 |
| 4,323,358 | 4/1982 | Lentz et al. | 8/94.11 |
| 4,378,224 | 3/1983 | Nimni et al. | 8/94.11 |
| 4,383,832 | 5/1983 | Fraefel et al. | 8/94.11 |
| 4,389,487 | 6/1983 | Ries | 435/273 |
| 4,402,697 | 9/1983 | Pollock et al. | 8/94.11 |
| 4,405,327 | 9/1983 | Pollock et al. | 8/94.11 |
| 4,526,751 | 7/1985 | Gartner | 422/37 |
| 4,647,283 | 3/1987 | Carpentier et al. | 623/11 |
| 4,648,881 | 3/1987 | Carpentier et al. | 623/11 |
| 4,729,139 | 3/1988 | Nashef | 8/94.11 |
| 4,753,652 | 6/1988 | Langer et al. | 623/1 |
| 4,798,611 | 1/1989 | Freeman, Jr. | 623/66 |
| 4,800,603 | 1/1989 | Jaffe | 8/94.11 |
| 4,801,299 | 1/1989 | Brendel et al. | 623/1 |
| 4,838,888 | 6/1989 | Nashef | 623/2 |
| 4,885,005 | 12/1989 | Nashef et al. | 8/94.11 |
| 4,946,673 | 8/1990 | Pollack et al. | 424/667 X |
| 4,969,912 | 11/1990 | Kelman et al. | 623/66 |
| 4,976,733 | 12/1990 | Girardot | 623/11 |
| 5,116,623 | 5/1992 | Khan et al. | 424/667 X |
| 5,137,718 | 8/1992 | Gilespie | 424/667 X |
| 5,227,161 | 7/1993 | Kessler | 424/667 X |
| 5,256,701 | 10/1993 | Tamura et al. | 424/667 X |

Primary Examiner—Randall L. Green
Assistant Examiner—Dinh X. Nguyen
Attorney, Agent, or Firm—Rosenblatt & Associates

[57] ABSTRACT

The present invention provides an iodine-based solution, and a method of using that solution, which sterilizes tissue implants without denaturing the proteins in the implant and without inducing calcification of the implant in vivo. Preferably, the tissue implants sterilized using the present invention are fixed without using glutaraldehyde. Most preferably, the tissue implants are fixed by photooxidation.

12 Claims, 11 Drawing Sheets

STERILIZATION OF TISSUE IMPLANTS USING IODINE

BACKGROUND OF THE INVENTION

Many types of implantable devices for repairing or improving the function of human body parts are known. Examples are vascular prostheses and grafts, tissue valves, and even completely artificial organs. The material that is used to make these implants or prostheses may be synthetic or it may be actual tissue derived from man or from some other species. For example, tissue implants often are derived from porcine or bovine sources. When an implant is made of actual tissue, the tissue may be used fresh from the donor; however, it is preferable to preserve the implant tissue for later use.

One primary obstacle to successful implantation of actual tissue implants is immune response against the implant by the recipient. Immune response against an implant is a result of antigenic differences between cells of the recipient and cells of the implant material. The recipient's natural immune response is to attack the foreign antigens on the cells of the tissue implant.

One widespread means used to overcome immune reactions against a tissue implant is to fix and preserve the tissue implant using glutaraldehyde before implantation. Theoretically, glutaraldehyde is believed to coat, bind and cross-link the antigens on the surface of the tissue implant. As a result, the number of antigens on the implant that are capable of inducing an immune response in the recipient are reduced.

Glutaraldehyde-preserved tissue implants are relatively inert biologically and have demonstrated long-term durability in some instances even though the glutaraldehyde renders them somewhat cytotoxic. However, glutaraldehyde treated implants also have demonstrated serious drawbacks, such as tissue-fatigue and a propensity toward calcification. Glutaraldehyde tends to leach out of a tissue implant into both the surrounding tissue and into the bloodstream. Also, because glutaraldehyde is cytotoxic, the cells exposed to the leached glutaraldehyde can be damaged. Cells damaged by glutaraldehyde often die and/or rupture. Dead and/or ruptured cells often serve as a nidus for calcification. In fact, calcification has proven to be one of the primary reasons for failure of glutaraldehyde-treated implants.

One solution to this calcification problem has been to fix and preserve tissue implants using photooxidation rather than glutaraldehyde. Photooxidation involves placing the tissue implant in saline, exposing the implant to a photocatalytic dye, and then subjecting the implant to fluorescent light. Photooxidation also modifies the structure of the collagen and appears to provide new cross-links in the collagenous tissue. However, implants that have been fixed using photooxidation do not exhibit the same tendency to calcify as glutaraldehyde-treated implants.

Although photooxidative fixing of tissue implants shows great promise, the implant still must be sterilized before it can be implanted in the recipient. Unfortunately, the most common method used to sterilize a tissue implant is to treat the implant with glutaraldehyde. Sterilization with glutaraldehyde, even after the tissue implant has been fixed, still could create a calcification problem. Therefore, it would be advantageous if tissue implants could be sterilized without using glutaraldehyde.

Historically, many germicidal or disinfectant solutions have been used to sterilize various objects and materials. The majority of such solutions have been used to disinfect solid surfaces. However, some disinfectant solutions have been used to disinfect soft surfaces, including human skin. Some of the disinfectant solutions previously used to sterilize human tissue, for example, the preparation known by the trademark "Betadine TM," have been iodine-based. Although iodine-based disinfectants have been used safely and effectively to sterilize the surface of living tissue, iodine-based solutions have not been used to sterilize non-living tissue such as the tissue found in a tissue implant.

Whether or not an iodine-based disinfectant solution can safely and effectively sterilize the non-living tissue in a tissue implant is a valid concern. Living tissue can survive relatively rigorous conditions because living tissue is capable of repairing any damage that may result from such conditions. In contrast, non-living tissue cannot repair itself. When the proteins in non-living tissue are subjected to rigorous conditions, they tend to denature. Denaturation of the protein in the tissue implant, which cannot be repaired by the non-living tissue, detrimentally affects the physical properties of the tissue implant.

A method of sterilizing tissue implants which does not cause protein denaturation and which does not induce calcification in vivo would be highly desirable.

SUMMARY OF THE INVENTION

The present invention provides an iodine-based solution, and a method of using that solution, which sterilizes tissue implants without denaturing the proteins in the implant and without inducing calcification of the implant in vivo. Preferably, the tissue implants sterilized using the present invention are fixed without using glutaraldehyde. Most preferably, the tissue implants are fixed using photooxidation.

BRIEF DESCRIPTION OF THE DRAWINGS

FIGS. 1-5 chart the results of the experiments discussed below.

FIG. 4 indicates sterilization conditions and charts the change in shrink temperature dependent upon the time of incubation and the presence (4B, 10%) or absence (4A) of ethanol.

DETAILED DESCRIPTION OF THE INVENTION

Figure 1A:
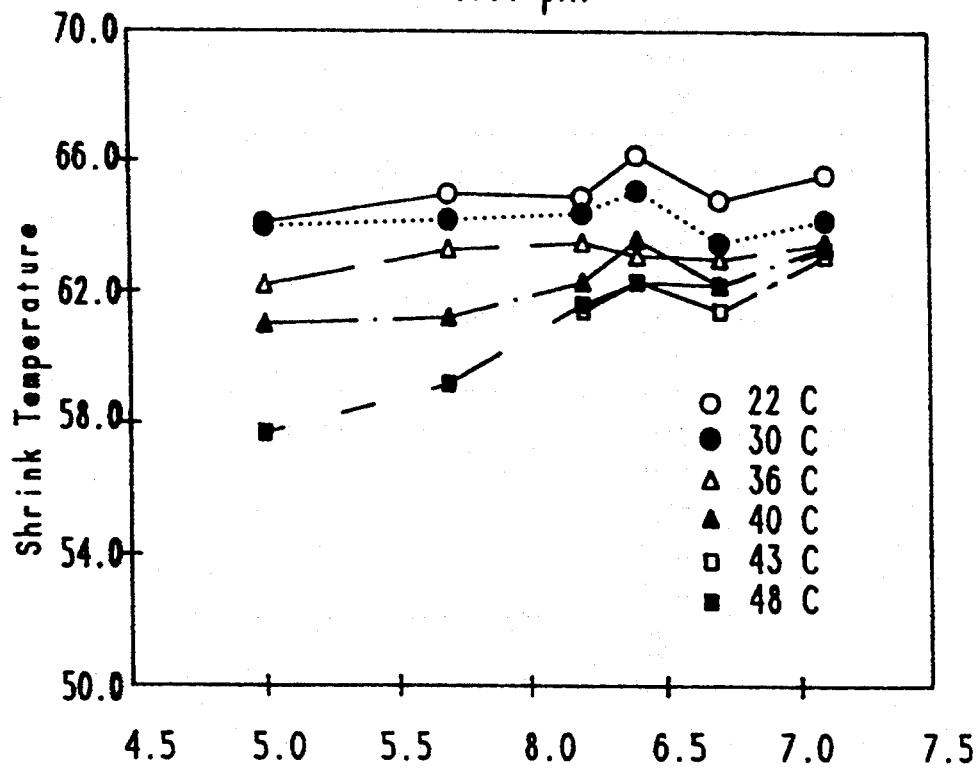
FIG. 1A indicates the temperature at which sterilization took place and charts the change in shrink temperature of a tissue implant dependent upon the pH of the iodine sterilant used.

The present invention involves the sterilization of tissue implants which preferably have not been treated with glutaraldehyde. Most preferably, the tissue implants used in the present invention will have been fixed photooxidatively using the procedure described in U.S. patent application Ser. No. 07/388,003.

In a preferred embodiment of the present invention, the tissue implants are sterilized using an iodine based germicidal solution under conditions having four primary variables: time of incubation; temperature of incubation; chemical content; and, pH of the germicidal solution. If any one of these four parameters is too stringent, the tissue implant may be damaged or the sterilization may be insufficient. Therefore, these parameters must be carefully controlled.

Although it is possible not to add stabilizing salts to the iodine based solution of the present invention, the solution preferably contains iodine stabilizing salts which are believed to help maintain the elemental iodine in a microbiocidal condition. A number of salts might be suitable for this function, preferably halide salts, and most preferably iodide salts, such as potassium and sodium iodide.

Another variable which tends to increase the microbial kill efficacy of the present solutions is to refresh the solution at approximately 24 hour intervals. If the solution is refreshed, solutions containing lower concentrations of iodine appear to be more efficacious.

In order to avoid damaging the tissue implants, as the stringency of any one of the following treatment parameters is increased within the following ranges, the stringency of the other parameters should be decreased:

| Parameter | Low | High |
| --- | --- | --- |
| elemental iodine (I2) | 0.01% | 0.20% |
| potassium iodide (KI) | 0% | 0.40% |
| sodium iodide (NaI) | 0% | 0.40% |
| ethanol | 0% | 20% |
| pH (aqueous solution) | 5.0 | 6.8 |
| NaCl | — | 4M |
| time of incubation | 3 hours | 2 weeks |
| incubation temperature | 20° C. | 50° C. |

A preferred embodiment of the present invention involves incubation of a tissue implant at a temperature between about 35°–39° C. for a period of time sufficient to sterilize the implant, typically between about 46–50 hours, in a solution containing between about 0.09–0.11% each of elemental iodine, potassium iodide, and sodium iodide and between about 1.8–2.0% ethanol, the solution having been buffered to a pH between about 6.4–6.6 using purified water and phosphate buffered saline. The ethanol content of the solution described in these preferred embodiments is a result of residual ethanol from the solution used to prepare the iodine stock. Although the present invention is functional if additional ethanol is present, no additional ethanol is added in these preferred embodiments.

A particularly preferred embodiment of the present invention involves incubation of the implant at approximately 37° C. for about two days in a solution containing about 0.1% each of elemental iodine, potassium iodide, and sodium iodide, about 1.9% ethanol, the solution having been buffered to a pH of about 6.5 using purified water and phosphate buffered saline.

In a preferred method of preparing the germicidal solution of the present invention, a concentrated (10X) phosphate buffered saline solution ("PBS") is prepared by combining about 76 gm NaCl, 35 gm $Na_2HPO_4$, and approximately 950 mL distilled or purified water (to a total volume of one liter), and stirring the resulting mixture until the ingredients are dissolved. Additional $NaH_2PO_4$ is added (approximately 13.6–14 gm) until the pH of the resulting solution is about 6.5. Unless otherwise specified, the chemicals used herein may be obtained from a number of commercial sources, such as Sigma Chemical Company, St. Louis, Mo., or Aldrich, 1001 West Saint Paul Avenue, Milwaukee, Wiss. 53233.

A preferred iodine stock solution is prepared by combining about 5.0 gm each of elemental iodine ($I_2$), potassium iodide, and sodium iodide, with about 100 ml of 95% ethanol which has been prewarmed to about 37° C. The mixture is swirled until the iodine is completely dissolved. The resulting solution may be stored in the dark for up to one month.

To prepare the solution for actual use to sterilize a tissue implant, the following should be dissolved in about 850 mL distilled or purified water in a 2 liter beaker or flask: about 100 mL 10X PBS stock solution; 20.0 mL 5% iodine stock solution. After all of the components have dissolved, the pH of the solution should be adjusted to about 6.5 using the appropriate sodium mono- and dibasic-phosphates, as needed. The solution then should be brought to 1.0 liter using additional distilled or purified water, as needed. The resulting solution should be filtered through a 0.2 micron sterilizing filter into a sterile container which may be capped, sealed, labeled, and stored at room temperature in the dark for up to a maximum of one week.

In order to sterilize a tissue implant using the foregoing iodine solution, the following preferred procedure should be performed within a laminar flow hood. All personnel should wear appropriate attire, including gowns, mask, hat, and sterile gloves. The following items should be placed within the laminar flow hood: sterile 5 inch forceps; clean plastic jars; prepared labels; prepared iodine solution. The implant container should be opened and the tissue implant and test sample or "swatch leaflet" removed using the sterile forceps. The containers should be opened one at a time and the transfer should be completed before another tissue implant is removed from another container. The tissue implant and swatch leaflet should be placed in a clean plastic jar (such as a 3 oz. polypropylene jar) and the prepared iodine sterilant should be poured into the jar until the solution completely covers the valve (approximately 100 mL). The Jars containing the implant, the test swatch, and the iodine solution should be closed tightly and the outside of the jar should be wiped with a lint free cloth and ethyl alcohol and labelled. Two empty jars then should be filled with approximately the same volume of iodine and labeled as controls, and all of the jars should be placed in an incubator which has been calibrated to the desired temperature, preferably about 37° C., and incubated for 48±2 hours, or for 24 hour increments after which the iodine solution was refreshed.

After incubation, the jars should be removed from the incubator and placed in the laminar flow hood, along with a sterile five inch forceps, clean plastic jars, labels, and sterile 50% ethanol. The container should be opened and the tissue implant and swatch leaflet removed from the iodine/ethanol solution using the sterile forceps. The containers should be opened one at a time. The implant should be placed into one clean jar and the swatch leaflet placed into another, and 50% ethanol should be aseptically poured into the jars until the implant and the swatch leaflet are covered completely (approx. 100 mL). The jars then should be closed tightly, and the outside of the jar should be wiped with a lint free cloth and ethyl alcohol and labeled. Two control jars for later sterilization testing then should be prepared by filling two empty jars with approximately the same volume of 50% ethanol and labeling the jars "control."

As an alternative to removing the tissue implant and swatch leaflet from the sterilization solution, it also may be possible to simply leave the implant and leaflet in the same solution for shipping, or to add ethanol to the sterilization solution without changing containers or removing the sterilization solution.

Tissue implants that have been treated according to the foregoing preferred method should be sterile and ready for implantation. The foregoing preferred parameters were derived as a result of three basic types of tests. A first type of test measured the biophysical integrity of the tissue implant after sterilization according to the present invention. Another type of test measured the biochemical integrity of the tissue implant. A third type of test measured the effectiveness of the regimen in sterilizing the implant. A fourth type of test involved actual implantation and monitoring of the implants.

A simple examination with the naked eye is capable of detecting some biophysical damage to tissue, e.g., damaged tissue Generally appears tough, leathery, or curled. Another, more precise method of measuring biophysical integrity is a "shrink" test.

Shrink tests are based on the following phenomenon. When bovine or porcine tissue is placed in water and heated, healthy tissue typically begins to shrink or shrivel at a temperature of around 62° C. If the tissue has lost integrity or been damaged in some way, e.g., by exposure to acid, the damaged tissue will begin to shrink at a lower temperature. The "shrink temperature" ($T_s$), or the temperature at which the tissue begins shrinking, can be measured by extending the tissue between the two ends of an extensometer and measuring the temperature at which the tissue begins to shrink.

In addition to shrinking at lower temperatures, damaged tissue may exhibit several other symptoms: the thickness of the tissue may change; the tissue may become more susceptible to attack by destructive agents, such as proteases, other digestive enzymes or chemical agents; the tissue may exhibit leakage of tissue components, such as collagen; and, well-defined striation of the tissue may begin to disappear when the tissue is scanned with a transmission electron microscope. Thus, tests were conducted which: (1) measured the percent change in thickness of the tissue before and after treatment according to the present invention; (2) subjected the treated tissue to a solution containing the chemical digestive agent cyanogen bromide (CNBr), which is capable of digesting damaged tissue; (3) subjected the treated tissue to an assay for collagen extractability (PAGE); and, (4) subjected the treated tissue to scanning by transmission electron microscopy (TEM).

Tests also were conducted to measure how effective various treatment regimens were in actually sterilizing tissue implants. A tissue implant may be contaminated in three separate locations: the components of the implant; the germicidal solution, itself; and, the ethanol in which the implant is stored after it is sterilized. Each of these locations was tested for contamination after tissue implants had been sterilized using the present invention.

Finally, tissue implants which had been sterilized according to the present invention actually were implanted in juvenile sheep and later explanted and examined for integrity and evidence of calcification.

In most of the following tests, the sterilization solution was prepared by a slightly different procedure than the preferred procedure already described; however, the procedure resulted in the same sterilization solution. The variation in procedure involved adding the potassium and sodium iodides after the iodine stock solution had been formed. The iodine stock solution was prepared by combining the elemental iodine ($I_2$) with 95% ethanol which was prewarmed to about 37° C. The mixture was swirled until the iodine is completely dissolved. The sterilization solution then was prepared by dissolving in distilled purified water: the 10x PBS stock solution; the 5% iodine stock solution prepared as just described; sodium iodide; and, potassium iodide.

The following tests demonstrated that the present invention safely and effectively sterilized tissue implants without inducing the calcification normally seen in Glutaraldehyde-treated implants.

INTEGRITY TESTS

SHRINK TESTS

Incubation of bovine pericardial tissue in a composite iodine solution can result in altered shrink temperature characteristics. The following experiments indicated that only very mild conditions result in an unchanged shrink temperature value (typically 65°±2° C.). These conditions (e.g . 1 day in 0.1% iodine at room temperature) may be insufficient to provide an adequate sterilization process for a tissue valve. However, more extensive iodine treatment conditions (e.g. longer times, higher concentrations, higher temperatures) can lead to markedly lower shrink temperature values. Tissue exhibiting a $T_s$ in the 55° C. or lower range are visually altered, appearing thicker, curled, and discolored. Between these extremes exists a broad window of tissue treatment conditions. Many tissue treatment conditions presented here result in a lowering of shrink temperature values of only 2°–3° C., which may not indicate tissue damage. Beyond this plateau, lie more extreme conditions resulting in $T_s$ values from 55°–62° C. Note that even control solution treated tissue (no iodine) exhibits a 2°–3° C. drop in Ts values. Therefore, a similar drop in $T_S$ under iodine treatment conditions indicates the absence of any iodine mediated tissue damage.

Safe tissue treatment is arbitrarily defined here as resulting in tissue with a shrink temperature of 62° C. or greater. From the following experiments, one limit, or window, of safe tissue treatment is defined as a set of conditions (with a reasonable safety factor) with maximal parameter values of about:

0.1% iodine

37°±2° C. incubation temperature 4 days incubation, and pH 6.0 (minimum)

with the following acceptable additions of:

iodide salts

NaCl, or ethanol

The use of iodine as an effective sterilant depends on a suitable quality of tissue emerging after sterilization. If tissue presenting $T_S$ values above 62° C. is deemed acceptable, there exists a range of incubation conditions demonstrated here which have the properties of:

consistently resulting in this quality of tissue a reasonable safety margin for $T_S$ values, and an expectation of acceptable sterilization capabilities Experimental Procedure In the following experiments, photooxidized bovine pericardial tissue was destained to a light blue to remove excess photocatalyst, as might occur in tissue valve product, and cut into one inch squares by water jet before use. The tissue pieces were soaked in a total of 40–80 mL of iodine (or control) solution per square in a clean polypropylene jar. Iodine solutions were prepared as described above, with the PBS solution diluted to 1X PBS and the pH adjusted with monobasic potassium phosphate after iodide/iodine addition.

After incubation with iodine or control solutions, tissue samples were transferred to 50% ethanol/water and stored at 4° C. until analysis. Solution color and pH were noted. Tissue squares were cut into one-half by one inch rectangles and briefly hydrated with water at room temperature before initiation of a shrink test similar to those known in the art. See, e.g., Nimni, M. "Collagen: Structure, Function, and Metabolism in Normal and Fibrotic Tissues." *Seminars in Arthritis and Rheumatism*, Vol. XIII, No. 1 (August 1983), incorporated herein by reference; Flandin, F., Buffevant, C., and Herbage, D. "A Differential Scanning Calorimetry Analysis of the Age-Related Changes in the Thermal Stability of Rat Skin Collagen." *Biochimica et Biophysica Acta* 791 (1984) 205–211; and Le Louis, M. , et al. *Connect. Tiss. Rsch.* 9 (1982) 253–262, incorporated herein by reference.

The following procedure was performed. A water bath was filled to within 2" of the top, and the heater was turned on. Extensometers were plugged into their respective positions at the back of the tester. Each extensometer was mated with an appropriate channel, and a thermocouple and a computer supplied with an appropriate program were attached. The shrink tester program was retrieved and program prompts were followed for calibration, sample identification, and sample placement. To calibrate the minimum shrink, extensometer #1 was placed between the two rightmost calibration pegs such that the extensometer was firmly pressing against the sides of the pegs and the support on the bottom. To calibrate the maximum shrink, extensometer #1 was placed between the two outermost calibration pegs such that the extensometer was firmly pressing against the sides of the pegs and the support on the bottom. The calibration was made and the calibration curve was compared to the previous calibration curve. The curves were consistent; therefore, the samples were placed on the extensometers by penetrating one end of the samples with one side of the extensometer and then penetrating the other end of the samples so that the samples were pulled taut. The maximum desired test temperature was entered, and the extension of the sample was measured for each specimen. Then, the samples were immersed in the water bath and heated to the test temperature at a programmed rate.

The data reported here represents the inflection point of tissue shrinkage, i.e., the point where the tissue begins rapid shrink. Most data points represent duplicate measurements.

The following solution compositions for sterilants were used, and samples were treated at 42°±2° C. for 2 days, unless otherwise noted.

Solution B:
10% ethanol
0.1% iodine (each of NaI, KI, and $I_2$) in water

Solution C:
0.1% iodine (each of NaI, KI, and $I_2$)
1X PBS

Solution D:
10% ethanol
0.1% iodine
1X PBS

Note that the $I_2$ stock (50X) is prepared with 95% ethanol. Therefore, a 0.1% iodine solution contains an additional 1.9% ethanol. Also, residual ethanol invariably is carried over from the tissue samples to be sterilized (they are stored in 50% ethanol).

General Observations

Stability of pH

After transfer of the tissue samples to ethanol, the remaining iodine solutions were retained for color and pH analysis. It was found that the pH of buffered solutions lowered only slightly upon incubation, generally less than 0.1 pH units. The most dramatic shifts (0.3 pH units lower) were seen with samples incubated at an extreme of 42° C. for 16 days. These relative pH stabilities were encouraging signs as low pH has been shown to be harmful to the tissue, and projected sterilization regimens involved extended incubations.

Color of Iodine Solutions

A typical 0.1% iodine solution has a deep red color. After incubation under a variety of conditions, the color varies from the same deep red to clear or even a pale blue or green if dye-stained tissue is used. In the experiments described here, a general trend with respect to solution color was noted. The color of the iodine solution was more faded under incubation conditions of higher temperature, higher pH, and longer incubation time. Under an "average" set of conditions (Solution C), namely 0.1% iodine, pH 6.5, incubated at 42° C. for two days, solutions were a pale red/deep yellow. Earlier results supported a hypothesis that the remaining "redness" of the sterilant after specific incubation times was proportional to the killing effectivity of the solution. This does not indicate, however, that conditions leading to solution fading are necessarily detrimental since the total antimicrobial action of the solution may be sufficient regardless of the eventual iodine dissipation. In other words, it may not matter if the solution is clear after the incubation cycle as the solution (and product) already may be sterile.

Tissue Appearance

Tissue appearance may be used as a gross predictor of shrink temperature. Note that the following observations refer to tissue sample appearance prior to the actual shrink temperature analysis of those samples (shrink temperature determination is a destructive analytical tool which leaves tissue curled, tough, and approximately one-fifth of its original size). Samples exhibiting low shrink temperatures (below 55°–60° C.) tend to appear thicker, curled, less flexible, and sometimes darker. Samples with moderately low shrink temperatures (60°–62° C.) are difficult to distinguish from non-sterilized photooxidized tissue except for iodine staining (which is reversible upon storage in 50% ethanol). In these experiments, conditions leading to low shrink temperature also resulted in more dramatic tissue changes. Conditions of higher temperatures, lower pH, higher iodine levels, and longer incubation times resulted in darker, more rubber-like tissue samples.

Shrink Temperature Measurement

Shrink test data were gathered as described. Control samples, either fresh or photooxidized, but not treated with any iodine solution, typically exhibited a shrink temperature inflection at 66°±2° C. These data are not shown; however, note control samples in various experiments which were incubated in solutions and treated under sterilization conditions in the absence of any iodine (shown with individual experiments as no iodine) or not incubated (shown as t=0 data).

Percent Change of Thickness Measurement

The percent change of thickness of the tissue was measured by first ensuring that, without a sample present (resting state), the thickness gauge (Federal Products, Providence, RI, Model 691B-R2 equipped with 50 g total load) reads 0±0.0001 inch. The gauge lever then was depressed to raise the load face. With the lever depressed, the flattened, unwrinkled sample was placed under the load face and on top of the load platform. The lever was raised until the face fully rested on the sample. The load was allowed to settle on the tissue for a period of thirty seconds, and the reading was recorded.

Experiment 1

Figure 1B:
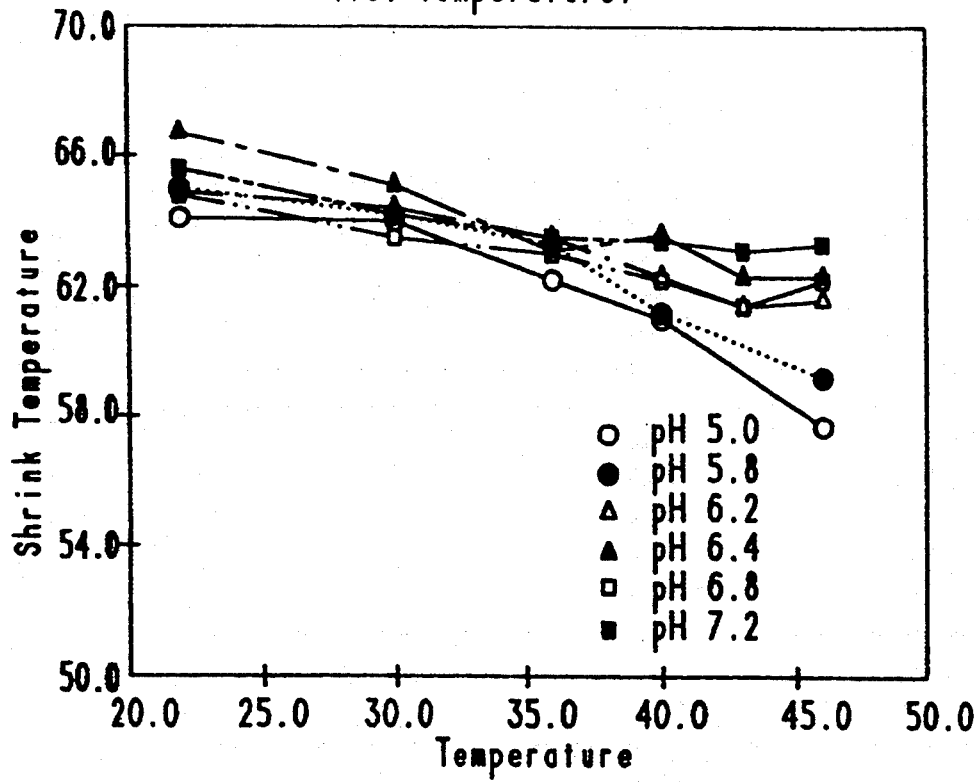
FIG. 1B indicates the pH at which sterilization took place and charts the change in shrink temperature of a tissue implant dependent upon the temperature at which the sterilization procedure took place.

Parameters
Incubation time=2 days
No ethanol
Incubation temperature=23°, 30°, 37°, 40°, 43°, or 46° C.
pH=5.0, 5.8, 6.2, 6.5, 6.8, or 7.2
iodine level=0.1%
36 samples In this initial parameter study, one piece of tissue was incubated per 40 mL solution for 2 days at one of six temperatures (listed above), and at one of six pH values (listed above). These solutions were made in the absence of any ethanol. As seen in FIG. 1, there is a general trend towards lower shrink temperatures with higher temperatures or lower pH values. The samples incubated at 43° C. in the two lower pH solutions were severly curled and rubbery and shrink temperature analysis yielded no useful data.

Experiment 2

Figure 2A:
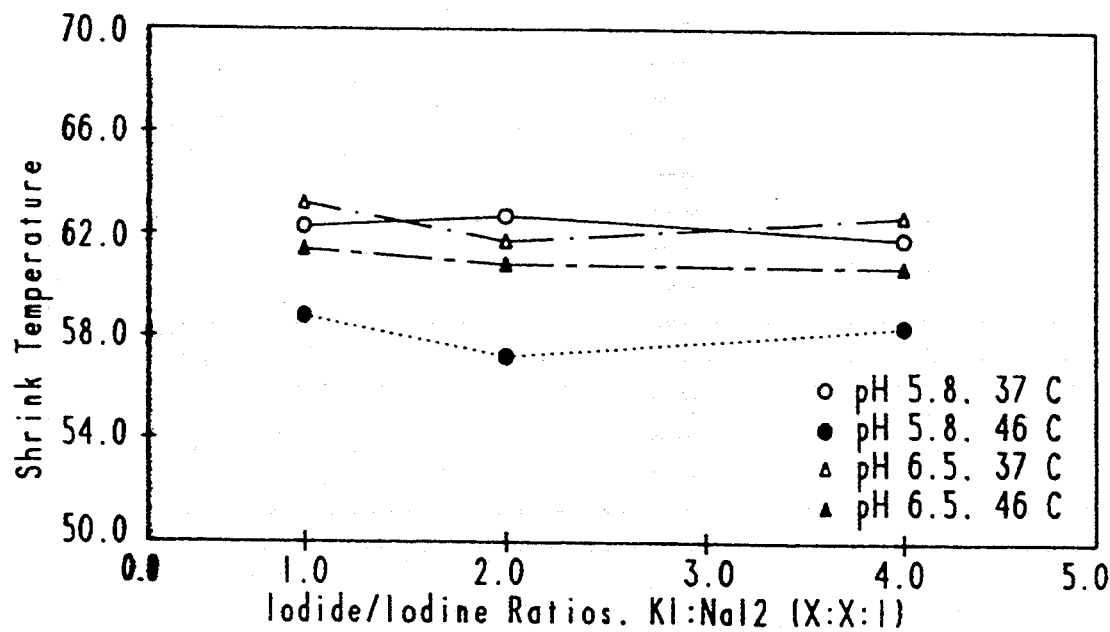
FIG. 2A and 2B compare shrink temperatures, when ethanol was either present (2B, 10%) or not present (2A) in the solution used to sterilize the tissue implants, as a function of iodide:iodine ratios present in the sterilant.
Figure 2B:
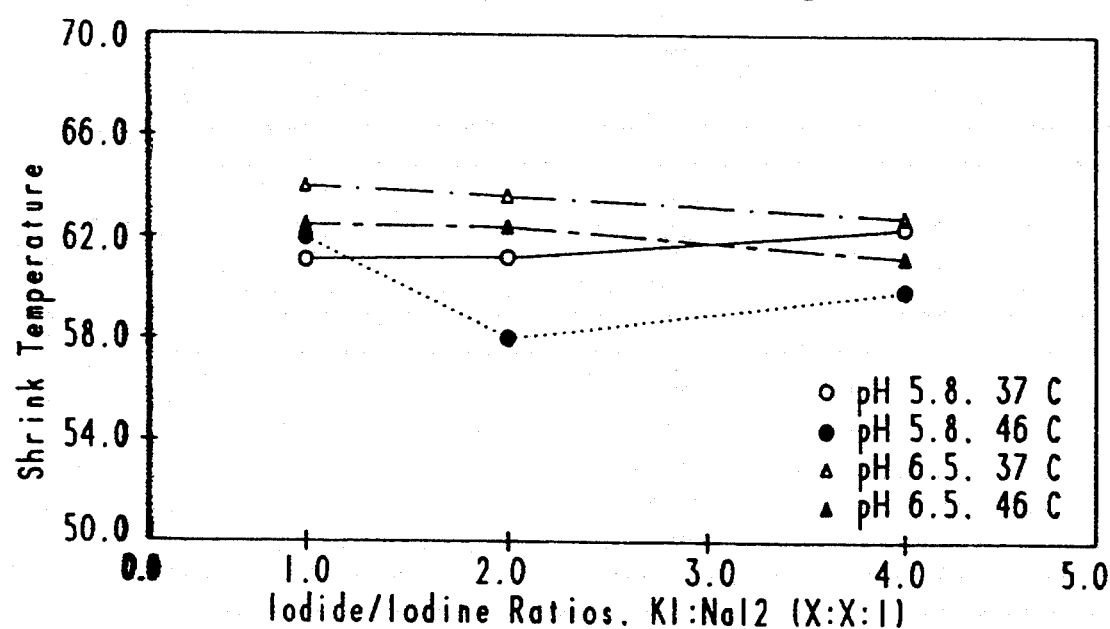

Parameters
t=2 days
±ethanol
temp.=37° or 46° C.
pH=5.8 or 6.5
$NaI:KI:I_2$=1:1:1, 2:2:1, or 4:4:1
$I_2$=0.1%
24 samples These samples were tested to determine the effect, if any, of additional iodide salts on tissue. It was hypothesized that additional iodide salts might help to establish an equilibrium in which elemental iodine remained in an antimicrobial form. Thus, lower levels of total elemental iodine might be used to effect the same antimicrobial activity in the presence of additional iodide salts. Commercial tincture of iodine solutions typically have an iodide/iodine ratio exceeding unity. Also, the extra salt (higher ionic strength) might have an additional protective effect on the tissue. However, as seen in FIG. 2, additional iodide salts exerted no apparent protective effect on tissue. Likewise, no negative effects were noted. If deemed necessary, the use of these increased ratios of iodide/iodine would not be expected to harm the tissue and in fact might provide a more effective iodine sterilant.

The color of different iodine solutions indicated a retention of iodine color at higher iodide levels, although these solutions were only slightly more intense in color (in 5 of 8 "sets," the highest iodide-containing solutions were the most colored, less colored in one, and indistinguishable in the other two). This might indicate increased stability of elemental iodine in the presence of additional iodide salts. However, incubation temperature was much more of a determinant in the final color of the sterilant, with those solutions incubated at a higher temperature being less colored in all cases.

Experiment 3

Figure 3A:
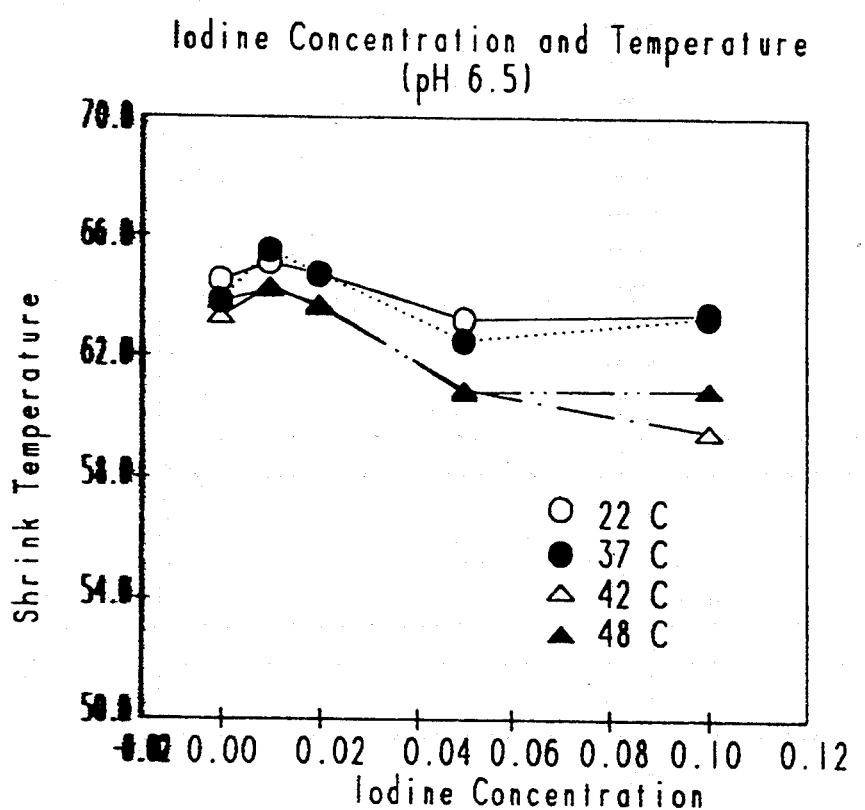
FIG. 3A charts the change in shrink temperature dependent upon the iodine concentration in a sterilization solution that has been buffered to a pH of 6.5.
Figure 3B:
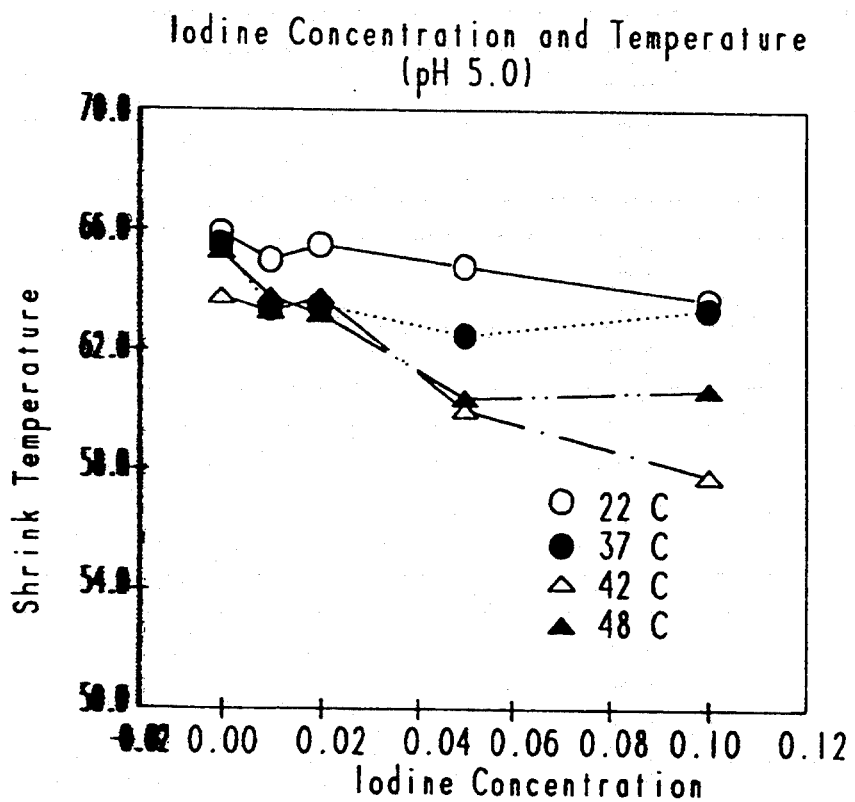
FIG. 3B charts the change in shrink temperature dependent upon the iodine concentration in a sterilization solution that has been buffered to a pH of 5.0.
Figure 3C:
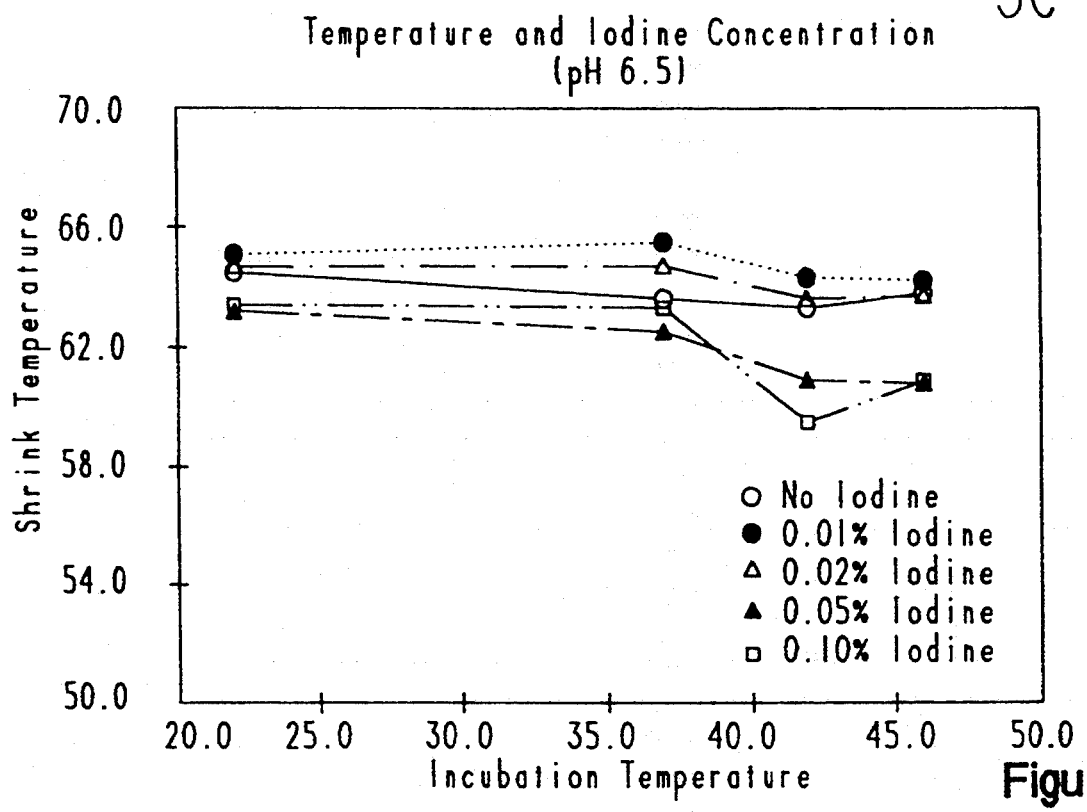
FIG. 3C charts the change in shrink temperature dependent upon the incubation temperature used with sterilization solutions having various iodine concentrations and which have been buffered to a pH of 6.5.
Figure 3D:
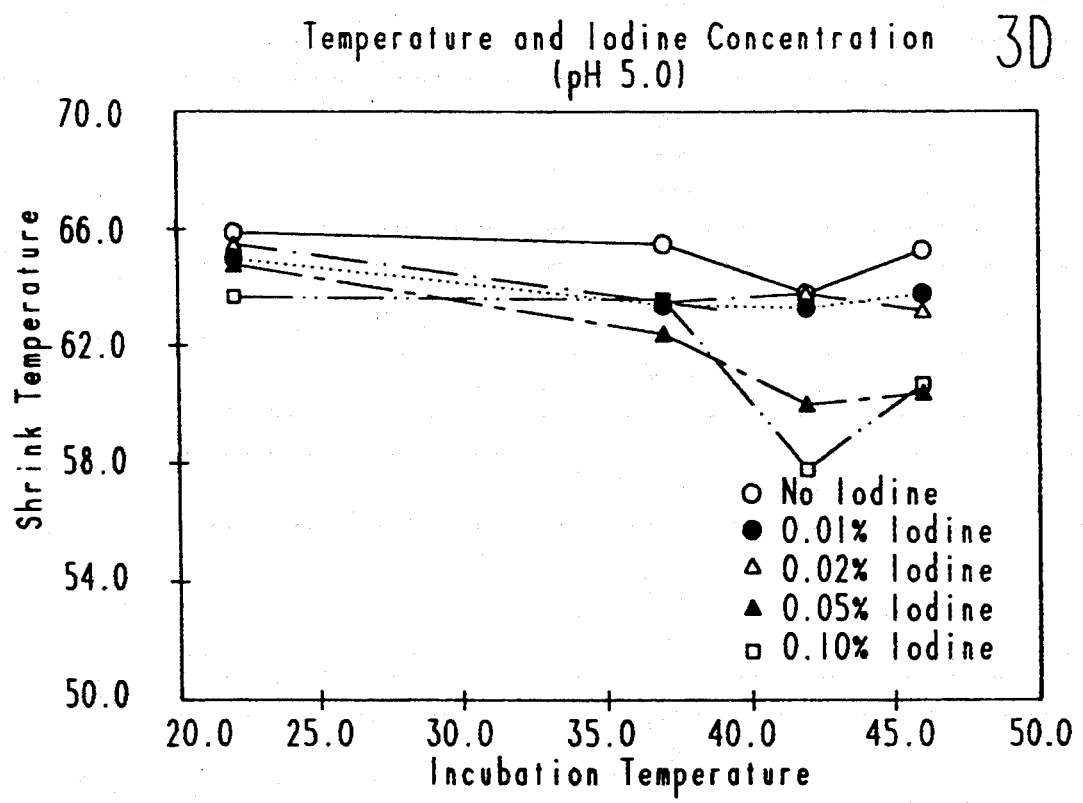
FIG. 3D charts the change in shrink temperature dependent upon the incubation temperature used with sterilization solutions having various iodine concentrations and which have been buffered to a pH of 5.0.

Parameters
t=2 days
iodine=0, 0.01, 0.02, 0.05, or 0.1% (each)
temp.=23°, 37°, 42°, or 46° C.
pH=5.0 or 6.5
40 samples (includes 0% iodine controls This experiment focused on the treatment of tissue with lower amounts of iodine. The ratio of iodide salts to iodine remained at 1:1:1. To correspond with lower iodine levels, other parameters were adjusted to test the limits of tissue stability, namely higher temperature and lower pH, both of which should have lead to greater microbial activity. As seen in FIG. 3, there was a gradual decrease in shrink temperature values as the levels of iodine increased. These values remained stable at pH 6.5 at all iodine levels up to 37° C., yet fell below 62° at 43° C. or above (FIG. 3A). The same statements can be made concerning the pH 5.0 samples although there was a sharper drop in values (FIG. 3B). FIGS. 3C and D, in which the same data was plotted vs. incubation temperatures, reemphasize the drop in shrink temperature at elevated temperatures. Again the effect was seen to be more dramatic at pH 5.0 (FIG. 3D).

Experiment 4

Parameters
time=0, 1, 2, 4, 8, or 16 days
temp.=22°, 37°, or 42° C.
pH=5.8 or 6.5
iodine=0.1%
ethanol=±10% added
72 samples+controls (no iodine)

Figure 4A:
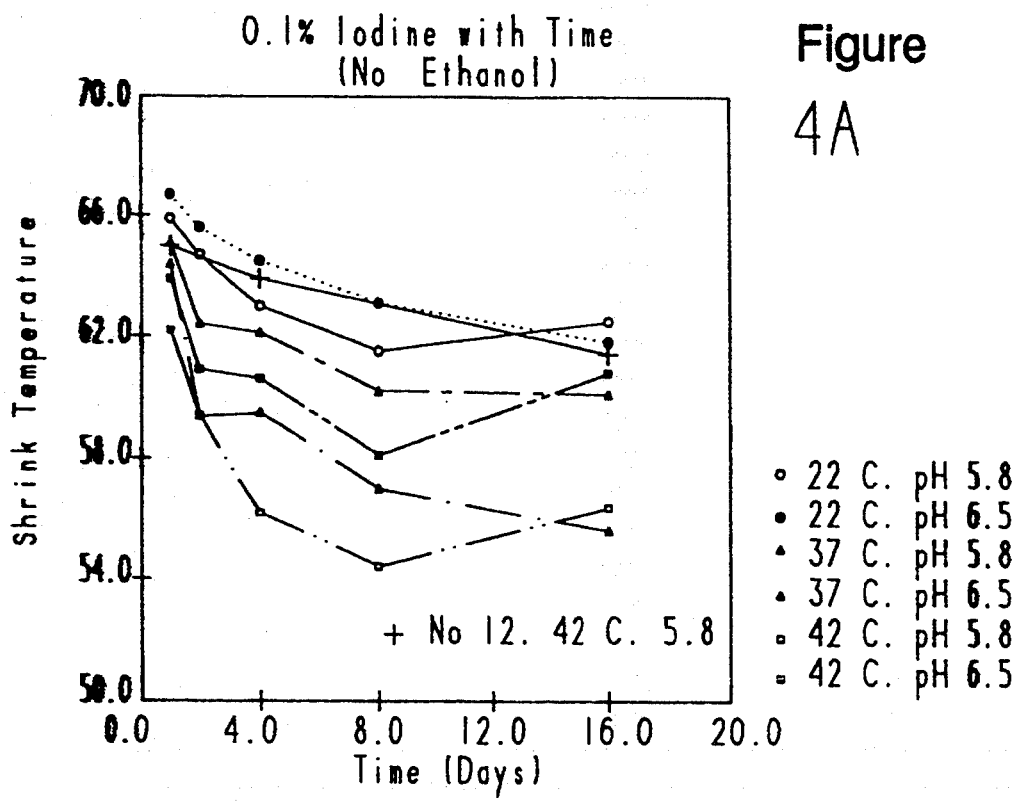
Figure 4B:
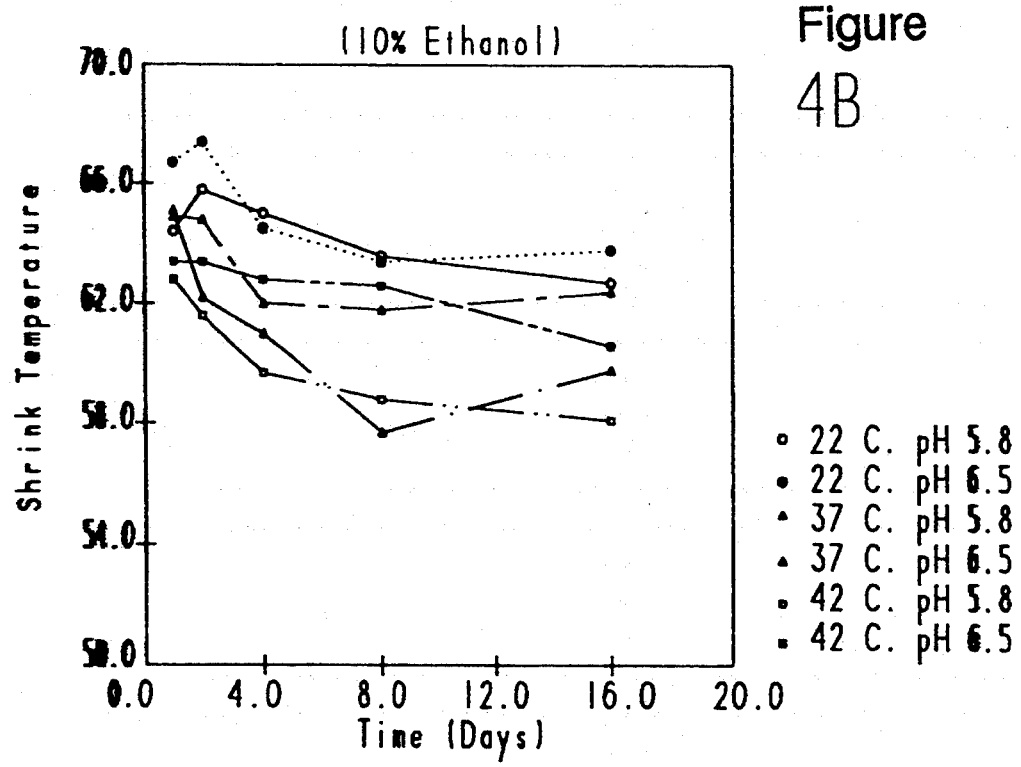

"Milder" parameters with respect to tissue shrink temperature effects (lower temperature and higher pH) might not lead to optimal antimicrobial activity. However, extending the time of iodine exposure might counterbalance this effect. This experiment was designed to test the effect of extended exposure to a variety of iodine solutions on tissue shrink temperature. FIGS. 4A and B indicate a decline in values over time under most conditions tested. The negative effects were less dramatic in the presence of ethanol, suggesting a protective effect. However, earlier experiments have indicated a lower kill effectivity in the presence of alcohol. Note, however, that the conditions under which this effect was most pronounced were those least likely to be employed, i.e., lower pH and higher temperature. In addition, these conditions lead to generally lower shrink temperatures overall.

The results of the control solution (in FIG. 4A, no iodine) containing no iodine at pH 5.8 leads to two conclusions. First, the presence of iodine itself can cause a lower shrink temperature value (vs. the control) and, secondly, there is a 2-3 degree drop in $T_s$ which apparently is caused by the buffer and incubation conditions alone, and not by the iodine. This drop in $T_s$, which is unrelated to iodine, may indicate that a 2-3 degree change does not represent any tissue damage (it certainly does not reflect iodine-induced tissue damage) and, furthermore, may be inconsequential in regards to tissue performance. Therefore, under carefully controlled conditions where, in the presence of iodine, there is a drop of 2-3 degrees there also may be no reason to suspect any tissue damage.

Experiment 5

Parameters
[NaCl]=2.5, 3.0, 3.5, or 4.0M
pH=5.0, 5.5, 6.0, 6.5
temp.=23° or 40° C.
iodine=0.1%
32 samples+controls Collagen stability is known to increase under high salt conditions. This experiment was designed to test whether high ionic strength solutions had any protective effect on the tissue. Similar shrink temperature values were obtained regardless of salt levels (from 2.5-4.0M). Overall, the values were lower with tissue incubated at 40° C. and little effect was seen with pH differences. In summary, high salt did not reverse or prevent the typical 2-3 degree drop in shrink temperature that was predictable for 0.1% iodine incubation for 2 days. Neither did high salt negatively impact shrink temperature values. Since no negative control (no salt) was included, it was difficult to directly assess whether the salt had a protective effect at a lower pH (5.0 & 5.5). However, comparison with results from previous experiments at lower pH values indicates that the salt may have had a slight protective effect.

Experiment 6

TEM Analysis

Figure 5A:
FIG. 5A is a transmission electron micrograph of collagen which has been damaged by treatment with iodine at a relatively low pH (3.5) and high temperature (42° C.).
Figure 5B:
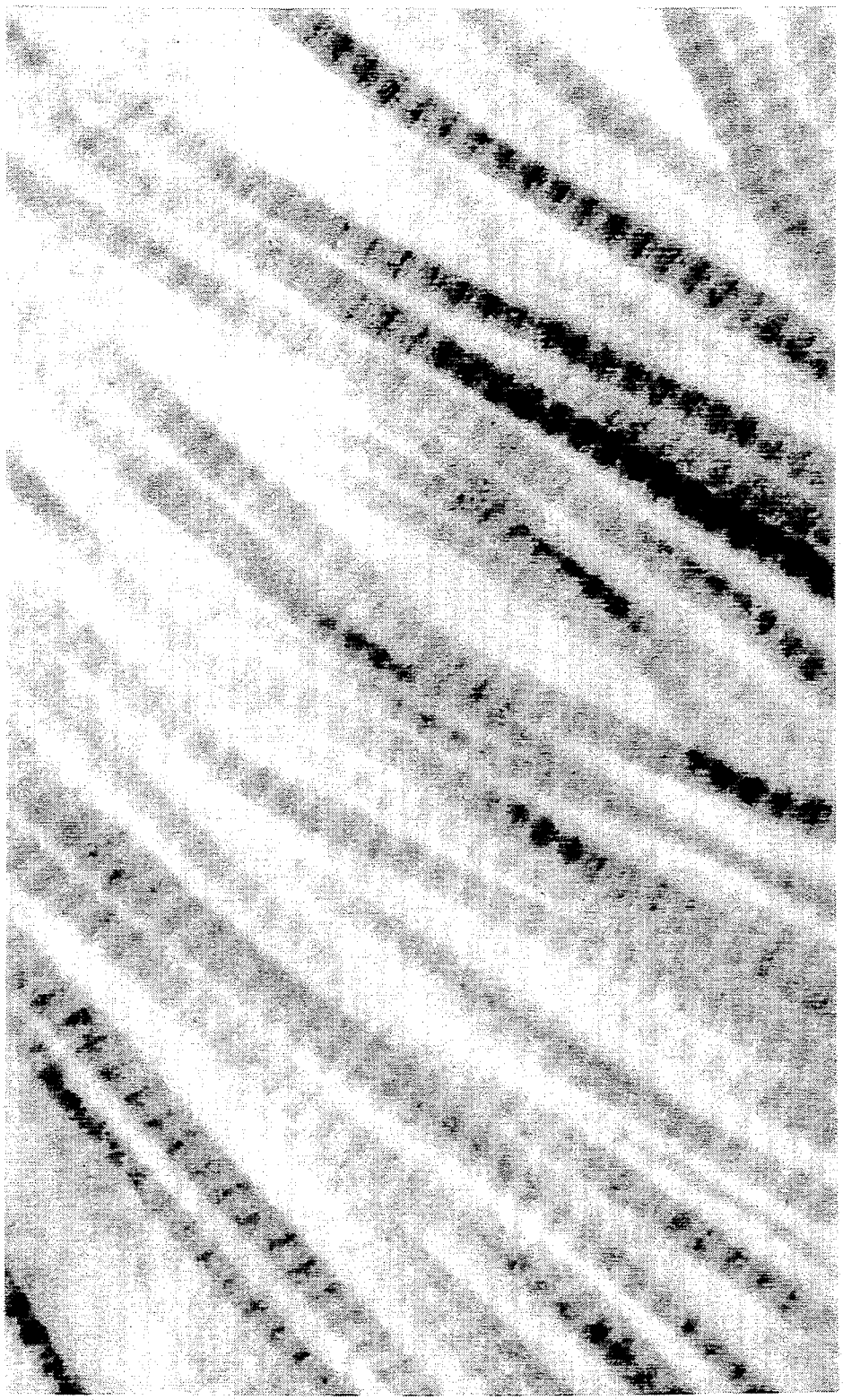
FIG. 5B is a transmission electron micrograph of substantially undamaged collagen treated with iodine at a pH of 6.5 at 42° C.

Transmission electron micrographs of tissue treated according to the present invention were obtained using known procedures, and the results are shown in FIG. 5. FIG. 5 graphically illustrates the potential harm of an extreme iodine sterilant. FIG. 5A shows a tissue treated in Solution B (pH ~3-5, 0.1% iodine, 2 days, 42° C.). Note the unravelling of collagen fibrils indicating severe base tissue damage. Contrast this to tissue in FIG. 5B, representing tissue treated using the following parameters, in which the collagen fibrils appear intact:

Parameters
0.1% iodine
pH 6.5 (PBS buffered)
"no" ethanol (except 2% from iodine stock and residual from tissue)
2 days incubation at 42° C.

Despite these results, this condition may not be desired due to its proximity to the "shrink temperature ledge".

Experiment 7

Animal Implants

Prior to discovering apparent tissue damage by Solution B (pH ~3.5, 0.1% iodine, 2 days, 42° C.), several valves were sterilized by this method and implanted in sheep. Accompanying tissue swatches revealed shrink temperature data for this tissue of 58°-60° C. for three of these valves and a value of 65° C. for the other. One of these animals (with an accompanying swatch $T_s$ of 58.3) died of unknown cause at day 66. Three animals were sacrificed and all of the valves looked to be in excellent condition with slight tissue stretching at 5 months. Angiography of each animal prior to sacrifice indicated physiologic performance for all valves with no regurgitation. The accompanying tissue swatches for these animals exhibited shrink temperatures of 59.6°, 59.4°, and 65.8° C., respectively. Thus, despite some signs of tissue damage, Solution B treated valves appeared to perform adequately in vivo.

DIGESTION AND LEAK TESTS

Experiment 8

In the following experiment, a 0.1% iodine solution was effective as a sterilant against $1 \times 10^7$ B. subtilis spores in the presence or absence of tissue valve components, while a 0.01% iodine solution was effective only in the absence of components. The effect on the tissue appeared to be minimal, with only a slight decrease in shrink temperature values and little effect on cyanogen bromide digestion, protein extractability, or tissue thickness. Most components were stained by the iodine solutions, although this appears to be reversible upon storage in 50% ethanol.

Two separate iodine sterilization solutions were used in the following experiments:
Condition 1:
0.1% iodine
phosphate buffered to pH 6.5 incubation at 37°±2° C.
incubation for 48±2 hours
Condition 2:
0.01% iodine
phosphate buffered to pH 6.0
incubation at 42±2 hours
incubation for 48±2 hours After incubation, samples were aseptically transferred to sterile filtered 50% ethanol.

The materials used in the incubations were dictated by the expected quantities and types of materials found in a completed tissue valve, which include: photooxidized bovine pericardial tissue; photooxidized porcine pericardial tissue; silastic; Reemay cloth; Dacron cloth; Elgiloy; polypropylene jars and lids; iodine solution; sutures (Gore-Tex and Green); valve holders; and, Teflon tags. The following types of tests were performed:
 material appearance of valve components (including jar and solution),
 cyanogen bromide (CNBr) digestion of tissue,
 collagen extractability of tissue (bovine and porcine),
 thickness measurement of bovine tissue,
 shrink temperature analysis of tissue (both),
 sterility of the iodine sterilants,
 sterility of the tissue samples,
 sterility of the ethanol storage solution, and
 sterility of the control solutions.

Table 1 reflects the conditions of each sample. A "+" under the column entitled "Inoculated" indicates prior spore inoculation with $10^7$ *B. subtilis*. A "+" under the column entitled "Components" indicates the presence of tissue valve components. A "−" under either column indicates, respectively, the absence of prior spore inoculation or tissue valve components:

TABLE 1

| Sample | Condition or Solution | Inoculated | Components |
|---|---|---|---|
| 10 | Condition 1 control (no iodine or iodide salts, pH 6.5) | − | + |
| 11 | Condition 1 (0.1% iodine) | − | + |
| 12 | Condition 1 (0.1% iodine) | − | + |
| 13 | Condition 1 (0.1% iodine) | − | + |
| 14 | Condition 1 (0.1% iodine) | − | + |
| 15 | Condition 1 (0.1% iodine) | − | + |
| 16 | Condition 1 (0.1% iodine) | + | + |
| 17 | Condition 1 (0.1% iodine) | + | + |
| 18 | Condition 1 (0.1% iodine) | + | + |
| 19 | 50% ethanol (RT inc.) | − | + |
| IC+ | Condition 1 (0.1% iodine) | + | − |
| IC− | Condition 1 (0.1% iodine) | − | − |
| 20 | Condition 2 control (no iodine or iodide salts, pH 6.0) | − | + |
| 21 | Condition 2 (0.01% iodine) | − | + |
| 22 | Condition 2 (0.01% iodine) | − | + |
| 23 | Condition 2 (0.01% iodine) | − | + |
| 24 | Condition 2 (0.01% iodine) | − | + |

TABLE 1-continued

| Sample | Condition or Solution | Inoculated | Components |
|---|---|---|---|
| 25 | Condition 2 (0.01% iodine) | − | + |
| 26 | Condition 2 (0.01% iodine) | + | + |
| 27 | Condition 2 (0.01% iodine) | + | + |
| 28 | Condition 2 (0.01% iodine) | + | + |
| 29 | 50% ethanol (42° C. inc.) | − | + |
| 2C+ | Condition 2 (0.01% iodine) | + | − |
| 2C− | Condition 2 (0.01% iodine) | − | − |

Cyanogen bromide digestion:
Cyanogen bromide digestion was conducted as follows:
 Reduction with 2-mercaptoethanol The amount of ammonium carbonate (Sigma A 8045) required for a 1M solution was calculated as follows: (78.06 gm/mol)×(1 mol/1)×final volume=gm of ammonium carbonate The calculated amount was added to 80% of the final volume of water and mixed on a stir plate until dissolved. The volume was measured in a graduated cylinder, and water was added to bring to the final volume and the resulting solution was mixed by inversion. The solution may be stored at 4° C. in a tightly capped container. Tissue samples were cut to the desired size (typically 4×6 mm) using a scalpel, and weighed on a Mettler analytical balance. The weight values were recorded (typically 20–30 mg.), and each piece was placed in approximately 1 ml of Ozarka distilled water in a microcentrifuge tube for rinsing.

The previously incubated tissue samples were transferred to clean microcentrifuge tubes, and to each tissue sample tube was added: 0.65 ml water, 0.1 ml 1M ammonium carbonate, and 0.25 ml 2-mercaptoethanol, to a final volume of 1 ml and a final concentration of 0.1M ammonium carbonate and 25% 2-mercaptoethanol (BioRad 161-0710). A desired amount (1 ml or less) of soluble collagen also was dispensed in microcentrifuge tubes. The same amount of ammonium carbonate and 2-mercaptoethanol was added to the soluble collagen, the final volume then was brought to 1.5 ml with water to result in the same final concentrations. All of the tubes then were incubated in a water bath at 55° C. overnight.

Removal of 2-mercaptoethanol

The 2-mercaptoethanol was removed from the samples as follows:
 Tissue Samples

Each tissue sample was rinsed three times in ~5 ml 60% ethanol, or until the 2-mercaptoethanol odor was gone.

Preparation of cyanogen bromide

Cyanogen bromide stock solution was prepared by placing a bottle of cyanogen bromide (Sigma C 6388) in the fume hood. (Note: CNBr is extremely toxic and should be kept in the hood at all times. Protective clothing and eyewear should be worn when handling CNBr.) 70% formic acid was prepared using the following formula:
 (a) (0.70)(final volume)÷0.99=volume of 99% formic acid (b) (final volume)−volume of 99% formic acid=water (c) combine 99% formic acid and water.

The 70% formic acid was added to the bottle for a concentration of 1 gm/ml (e.g., add 1 ml 70% formic acid to 1 gm CNBr). A tiny stir bar was placed in the bottle and the solution was stirred on a stir plate in the hood until the solid had dissolved.

The tissue pieces were transferred to 7 ml white-capped plastic tubes. A desired amount of the soluble collagen samples (0.43 ml or less) was transferred to a clean microcentrifuge tube.

The required amount of cyanogen bromide working solution was calculated by adding the weight (mg) of all samples for CNBr digestion (A) and multiplying the total value by five (5). The final concentration of each sample in solution should be 10 mg sample/ml. The required volume of working solution was calculated by dividing $A/10$ mg/ml=$X$ ml.

The CNBr working solution (50 mg/ml CNBr in 70% formic acid) was prepared, with 10% extra solution to insure an adequate amount, by determining X, Y, and Z, as described below, and multiplying by 1.1:

The required amount (ml) of 99% formic acid to make X ml of 70% formic acid was calculated using the following equation:

$$(0.70)(X \text{ ml}) \div (0.99) = Y \text{ ml}$$

The required amount of 1 gm/ml CNBr stock solution to make X ml of 50 mg/ml CNBr was calculated using the following equation:

$$(0.050 \text{ gm/ml})(X \text{ ml}) \div 1 \text{ gm/ml} = Z \text{ ml}$$

Y and Z were combined in a graduated 50 ml FALCON tube, and water was added to a total of X ml.

Digestion with CNBr

The working CNBr solution was dispensed into the sample tubes while maintaining a concentration of 10 mg sample/ml working solution (e.g., 3 ml CNBr working solution was added to a tissue piece weighing 30 mg using an Oxford 5 ml pipette). Each tube was capped tightly, placed in a test tube rack in the water bath, and incubated four hours at 30° C. The water bath was turned off and the tubes were incubated at room temperature overnight.

Similarly, 99% formic acid was added to the soluble collagen samples for a final concentration of 70% formic acid. E.g., using the following equation to calculate the amount of 99% formic acid to add for a final volume of 1.5 ml:

$$(0.70)(1.5 \text{ ml}) \div 0.99 = 1.06 \text{ ml}$$

An appropriate amount of CNBr stock solution was added for a CNBr:(soluble collagen) weight excess of 5:1. Water was added to reach the desired final volume and to maintain a constant soluble collagen concentration for each of the samples (e.g., 0.5 mg/ml). Each microcentrifuge tube was closed tightly and placed in a floating tube rack in the water bath. The tubes then were incubated for four hours at 30° C. The water bath was turned off and the tubes were incubated at room temperature overnight.

Dilution of Samples

Two microcentrifuge tubes containing 1.2 ml water each were prepared for each of the tubes containing a tissue sample. After overnight incubation, 200 ul of each sample tube was added to each of the 2 microcentrifuge tubes and the contents were mixed by inversion. A 400 ul liquid sample was drawn and the appearance of the tissue noted. The sample tubes were stored at −20° C.

Microcentrifuge tubes containing enough water for a 5- to 10-fold dilution were prepared for each tube containing soluble collagen. After overnight incubation, an aliquot of each sample containing enough protein to visualize in one lane of a polyacrylamide gel was added to each of the microcentrifuge tubes, and the resulting contents were mixed by inversion. The sample tubes then were stored at −20° C.

Freeze Drying of Diluted Samples

The Savant Speed-Vac SVC100 was placed in a fume hood and connected to a large (1 liter) Ehrlenmeyer flask using a vacuum tube and glass tubing inserted into a rubber stopper the size of the mouth of the flask. Another glass tube inserted into the same rubber stopper connected the flask to the vacuum pump with vacuum tubing. The flask was placed inside a styrofoam box, and the box was filled with dry ice. 2-propanol (99+%, ACS reagent grade) was added to create a cold slush around the flask. This is the cold trap, designed to freeze aqueous solutions under vacuum to avoid water accumulation in the vacuum pump oil. The cold trap was placed in the hood.

All microcentrifuge tubes were frozen in the cold trap. With their caps open, all tubes were placed in the rotor of the Speed-Vac and maintained in proper balance. The Speed-Vac was started. The vacuum pump was turned on, and a strong vacuum pull was ensured by checking the seal on the lid of the Speed-Vac. The samples were dried for several hours, or until all liquid was gone and only residue remained. The vacuum was released before stopping the Speed-Vac. ~1 ml water was added to each microcentrifuge tube, and each tube was vortexed and frozen again in the cold trap using the procedure just described. The residue of each set of tubes was combined as follows:

If more than one microcentrifuge tube existed per sample tube, 500 ul of water was added to the first microcentrifuge tube of the set and vortexed well. Everything in the first tube was transferred to the subsequent tube of each set, vortexing well between each transfer. If only one microcentrifuge tube per sample existed, 500 ul water was added and the contents vortexed. The samples then were freeze dried once again in the cold trap, as just described.

Sample Analysis

Dry samples were dissolved in water or buffer for analysis. If stored before analysis, the samples were stored at −20° C. The samples were analyzed by polyacrylamide gel electrophoresis.

Collagen Extractability 0.5M Tris-HCl, pH 6.8 and 10% SDS were prepared according to the BioRad PROTEAN II xi Slab Cell Instruction Manual (1990), incorporated herein by reference. 0.5% Bromophenol blue was prepared by dissolving 50 mg bromophenol blue in 10 ml of water purified using a MilliQ-UF filter system from Millipore Corp., Bedford, Mass. 2.5M NaCl was prepared by dissolving 7.3 gm NaCl in 50 ml MilliQ-UF water.

2X Sample Buffer (2X SB) was prepared by combining the following to form 10 ml total volume: 2 ml 0.5M Tris-HCl, pH 6.8; 2 ml 10% SDS; 2 ml glycerol; 0.4 ml 0.5% Bromophenol blue; and 3.6 ml MilliQ-UF water.

2 ml of extraction buffer was prepared as shown in the following chart:

Table 2 reflects the results of thickness measurement, shrink testing (T$_s$), CNBr digestion, and collagen extract assay testing for each sample:

TABLE 2

| | Bovine Leaflets | | | | Porcine Wrap | | | |
|---|---|---|---|---|---|---|---|---|
| Sample | Thickness (% Change) | Ts -Ave of 2 | CNBr | Extract Assay | Ts -Ave of 2 | CNBr | Extract Assay | pH >Inc* |
| 10 | −1.01% | 66.8 | P** | P | 67.7 | P | P | 6.60 |
| 11 | +0.46% | 65.3 | P | P | 64.8 | P | P | 6.40 |
| 12 | −1.14% | 66.0 | P | P | 66.7 | P | P | 6.42 |
| 13 | −0.22% | — | P | P | — | P | P | 6.40 |
| 14 | +0.21% | — | P | P | — | P | P | 6.40 |
| 15 | −0.79% | — | P | P | — | P | P | 6.41 |
| 19 | +0.25% | 65.3 | P | P | 65.9 | P | P | — |
| 20 | −0.42% | 64.8 | P | P | 65.4 | P | P | 6.11 |
| 21 | −0.24% | 64.7 | P | P | 65.3 | P | P | — |
| 22 | 0.23% | 63.5 | P | P | 64.2 | P | P | 6.08 |
| 23 | +0.53% | — | P | P | — | P | P | 6.09 |
| 24 | 0.00% | — | P | P | — | P | P | 6.08 |
| 25 | −0.21% | — | P | P | — | P | P | 6.08 |
| 29 | +0.21% | 65.2 | P | P | 64.3 | P | P | — |

*pH > Inc = pH after incubation.
**P = Passed test, i.e. exhibited lack of digested or extractable proteins.

| Sample | Final Conc. | Vol. (ml) |
|---|---|---|
| 2X SB | 0.05M Tris-HCl | 1.0 |
| | 1% SDS | |
| | 10% Glycerol | |
| | 0.01% Brom. bl. | |
| 2.5M NaCl | 1.0M | 0.8 |
| 2-mercaptoethanol | 4% | 0.08 |
| MilliQ H$_2$O | | 0.12 |
| | Total ml = | 2.0 |

Collagen extractability was measured by cutting and weighing a sample piece from each tissue type with average size being 4×8 mm. An untreated tissue sample was included as a control. Each tissue sample was rinsed in approx. 1 mL MilliQ-UF water in individual microcentrifuge tubes for 5–10 minutes and maintained on ice. The tissue pieces were patted dry with lint-free Kimwipes and weighed on an analytical balance (weight range=10–20±0.2 mg; no less than 8). The pieces again were transferred to clean, individual microcentrifuge tubes and kept on ice.

Two water baths were set up, one at 65° C. and one boiling. A portion of extraction buffer (0.5M acetic acid) was added to each microcentrifuge tube, maintaining a constant concentration of 160 mg tissue per ml of buffer. E.g., a 16 mg piece of tissue would receive an aliquot of 0.10±0.001 ml extraction buffer. The reaction tubes were tightly capped and placed in the 65° C. water bath for 20±0.25 minutes The extraction was stopped by placing all tubes directly on ice.] Equal aliquots of each sample (e.g. 30 ul per sample per gel lane) were removed and added to 30 uL of the 2x sample buffer in a separate 1.5 mL microcentrifuge tube. These tubes were tightly capped and placed in a floating tube rack in the boiling water bath for 3–5 minutes. The samples then were chilled on ice and loaded onto a gel and electrophoresed for 350 mA.hrs according to the methods described in PROTEAN II Dual Slab Cell Instruction Manual (Biorad Laboratories, Richmond, Calif.), incorporated herein by reference, using a 5–20% acrylamide gradient gel. The gel then was placed in a protein staining solution for approx. 1 hour and then destained until the colored background was clear.
Results:

Condition 1 solutions, whose sample number begins with a 1, initially had a pH of 6.5. Condition 2 solutions, whose sample number begins with 2, initially had a pH of 6.0.

The noted change in thickness is quite small and approximates experimental error for this technique. The shrink temperature values (Ts) indicate a drop of 1°–3° C. from controls (nonincubated leaflets) run in parallel; however, all shrink temperatures remain above 62° C. Therefore, the change is within acceptable limits. A P indicates a relative lack of detectable protein obtained through CNBr digestion when compared to digestion of nonphotooxidized tissue. Additionally, pretreatment of tissue with 2-mercaptoethanol prior to CNBr digestion resulted in tissue digestibility as seen with photooxidized controls. The collagen extraction assay resulted in a small quantity of unidentified lower molecular weight material, which was more prevalent with Condition 2 treated tissue. The final pH of all samples was within 0.1 pH units of the original solution, and therefore was acceptable.

Table 3 reflects the results of testing for microbial content. All of the samples listed, except 1C- and 2C-, were inoculated with 1×10$^7$ B. subtilis spores prior to the sterilization cycle. The components then were transferred to 50% ethanol. After one day in ethanol, the components were transferred to growth media and incubated for seven days to note any growth, indicating the presence of microorganisms. The iodine solutions and ethanol were filtered separately, and the filters were tested for microorganisms by submersion in growth media. In addition, a control media sample was inoculated to verify its ability to support microbial growth. A positive (+) indicates the presence of growth after seven days incubation while a negative (−) indicates no growth:

TABLE 3

| Sample | Components | Filtered Iodine | Filtered EtOH |
|---|---|---|---|
| 16 | − | − | − |
| 17 | − | − | − |
| 18 | − | − | − |
| 1C+ | − | − | − |
| 1C− | − | − | − |
| 26 | + | + | + |
| 27 | + | + | + |
| 28 | + | + | + |

TABLE 3-continued

| Sample | Components | Filtered Iodine | Filtered EtOH |
|---|---|---|---|
| 2C+ | — | — | — |
| 2C− | — | — | — |

ADDITIONAL MICROBIAL KILL TESTS

Experiment 9

The purpose of the following test was to compare the ability of two concentrations of iodine solution to kill spores of *Bacillus subtilis*. Of the bacteria used in microbial kill tests using chemical sterilants, *B. subtilis* is one of the most difficult to kill.

The results indicate that a 0.01% iodine concentration (Condition 2) was ineffective as a sterilant against spores of *B. subtilis* under the conditions of this test. Spores of *B. subtilis* survived in the 0.01% iodine solutions when incubated at 42° C. in the presence of the components of the final device. Growth of the inoculated organism occurred in all three jars tested under this condition. No growth was detected from a container of iodine that was inoculated with spores but without tissue valve components.

Although some Growth was noted in the *B. subtilis* samples, this does not mean that the solution failed to achieve a required kill rate. *B. subtilis* is one of the most difficult microorganisms to kill, and the *B. subtilis* samples were inoculated with $10^7$ spores. It should not be necessary to kill $10^7$ *B. subtilis* spores in order to pass regulatory standards.

Incubation with the higher concentration solution of iodine (0.1%, Condition 1) at an incubation temperature of 37° C. was effective to inactivate $10^7$ spores of *B. subtilis* per mL. All three jars tested using the 0.1% solution were sterile. The iodine solution alone, without components, also was sterile.

All of the media that was used in this study was shown to support growth of *B. subtilis*, the negative controls for growth were negative and the microbial air sample was negative for growth in the sterility laboratory. Of the organisms detected on a microbial air sample in the general laboratory, no evidence of *B. subtilis* was found.

It has previously been reported that the presence of organic matter may have an effect on iodine disinfection rates. For example, a 1:200,000 (0.0005%) concentration of iodine reportedly will kill wet spores in the absence of organic matter in 15 minutes. From the following study (and from Table 3), it appears that the presence of the organic tissue valve components do tend to lower the disinfecting activity of these iodine solutions, as previously reported.

Experimental Procedure

Components of a pericardial valve were incubated for 48 hours±2 hours, in the following two iodine solutions at different temperatures:

| Condition 1 | Condition 2 |
|---|---|
| 0.1% (w:v) $I_2$ | 0.01% (w:v) $I_2$ |
| 0.1% (w:v) NaI | 0.01% (w:V) NaI |
| 0.1% (w:v) KI | 0.01% (w:v) KI |
| 1X PBS | 1X PBS |
| ~2% EtOH (from iodine stock) | ~2% EtOH (same) |
| pH 6.5 | pH 6.0 |
| incubation T° = 37 +/− 2° C. | incubation T° = 42 +/− 2° C. |

Both iodine solutions were filtered with Nalgene Disposable Filterware, Lot #B10015, pore size 0.20u (cellulose nitrate filter). The excess ethanol was allowed to drip off of the components before placing them into the iodine solutions. Each jar was swirled by hand several times after closing the lid on the jar to be incubated.

Prior to incubation, both iodine solutions were placed in a laminar flow hood and inoculated with 0.1 mL ($10^7$) *B. subtilis* var niger spores obtained from North American Scientific Associates, Irvine, Calif., Lot#N16511, exp. May '92, $1.6 \times 10^7$ spores/0.1 ml. The spore suspension was vortexed for approximately 5 minutes and the suspension was viewed under 100× for evidence of clumping. No clumps were observed. The spore suspension was then verified. 0.1 mL of suspension was added to 9.9 mL of sterile water for injection to make $10^6$ spores/mL dilution. 1.0 mL of $10^6$ spores was added to 9.0 mL sterile water to get $10^5$ spores/mL. Further dilutions were made in a similar manner, to get $10^4$, $10^3$, $10^2$, $10^1$ spore concentrations using sterile test tubes and pipettes. 1.0 mL of $10^2$ spore dilution was spread onto 3 TSA plates. 1.0 mL of $10^1$ spore dilution was spread onto 3 TSA pates. All plates were incubated at 37°±1° C. for 48 hours. The number of *B. subtilis* colonies per mL were counted and the population count verified at an average of $1.3 \times 10^7$ spores/mL.

After inoculation, all jars were torqued closed to approximately 32-34 inch-pounds. The components then were transferred to approx. 80 mL of 50% ethanol which had been filter sterilized in the same manner as the iodine solutions and sterility tested. Sterility testing was performed by filtering through 0.45 u filter, rinsing with 100 mL of peptamin, and placing into 200 ml T-Soy Broth. No growth was observed after 7 days incubation at 35°±2° C.

After 24 hours in the 50% ethanol, the components, the iodine solutions, and the ethanol solutions were tested for sterility. The contents of each jar was filtered through a 0.45 u filter unit and placed into approx. 200 mL of T-Soy Broth and incubated at 35°±2° for 7 days and observed for growth. During in the hood sterility tests, a jar of media was left open continuously and closed upon completion of the test and incubated along with the other 3ars. After 3 days of incubation, no growth was observed in the media. Similarly, the forceps were dipped into 10 mL of T-Soy Broth which also was incubated at the same conditions. No growth was observed after 3 days.

Media Preparation

The solutions used in the procedure were prepared by the following methods:

0.1% PEPTONE WATER 1.0 g of peptamin (Bacto-Peptamin, USP XVII, DIFCO, Lot No. 796032) was mixed into 1.0 liter of distilled water. After mixing, the solution was dispensed in 100 ml quantities into milk dilution bottles and sterilized.

Control: One bottle from each sterilizer load was left at room temperature for 24 hours. No growth was observed from the Peptone Water.

TRYPTIC SOY BROTH (TSB)

30 g of dehydrated DIFCO Dehydrated Tryptic Soy Broth, Lot No. 801810 (exp. 10/96), was dissolved into 1.0 liter of distilled water. Approximately 200 ml of media was dispensed into pint mason jars and sterilized. Media was prepared and sterilized as per USP XXII Section 71, incorporated herein by reference. The pH of the media was 7.25.

Controls:
(A) A Growth Promotion Test was performed to show that the media was capable of supporting Growth of a low number of microorganisms. This test was done by inoculating <100 *B. subtilis* spores into one Jar of TSB. The medium was incubated at 35° C. *B. subtilis* Growth was confirmed on day three.

(B) All media was incubated for 24–48 hours at 35° C. No Growth was observed indicating the sterility of the media before the test began.

(C) Four jars of media were randomly chosen and incubated at 35° C. for the duration of the test. No Growth reconfirmed the sterility of the media.

TRYPTIC SOY AGAR (TSA) 20 g of DIFCO Dehydrated Tryptic Soy Agar, Lot No. 795207 (exp. 95), was mixed with 500 ml of distilled water, and steam sterilized. Within the biological safety hood, the media was poured into sterile 100×15 mm petri plates.

Control: *B. subtilis* was streaked onto one plate and incubated at 35° C. Growth on plate confirmed that the agar was capable of supporting growth.

Sterilization/Incubation

Solutions

Solution 1 and Solution 2 were prepared as previously described. The iodine solutions were filter sterilized through a 0.2 $\mu$filter unit. All white polypropylene jars used in this study were steam sterilized at 121° C. for 30 minutes. Each transfer was performed individually. First, the jar was filled with approximately 80 ml of the iodine solution. Then the components were aseptically transferred to the iodine solution. The lid was tightened. Once the transfers were complete, each jar (#16–18 and #26–28) was inoculated with $10^7$ *B. subtilis* spores. The inoculation was conducted outside the sterility testing laboratory within the biological safety cabinet. Jars were torqued to approximately 32–34 inch pounds. Jars 16–18 were incubated for 48±2 hours at 37°±2° C. Jars 26–28 were incubated for 48±2 hours at 42°±2° C.

Controls

Before use, the spore suspension was vortexed and viewed under a microscope for evidence of clumping. The spore population was verified by preparing serial dilutions to a $10^1$ spores/ml dilution and plating 1.0 ml onto triplicate TSA plates. The plates were incubated at 37°±2° C. for 48 hours. The number of colony forming units were counted, and the initial spore concentration was verified, as shown in Table 4:

TABLE 4

| Dilution | CFU/ml | No. spores/0.1 ml |
|---|---|---|
| 1:10$^6$ | 140 | 1.4 × 10$^7$ |
| 1:10$^7$ | 12 | 1.2 × 10$^7$ | average = 1.3 × 10$^7$ spores/0.1 ml
labelled = 1.2 × 10$^7$ spores/0.1 ml

Since the average spore population was determined to be 1.3×10$^7$ spores/0.1 ml and the labelled spore population was 1.6×10$^7$ spores/0.1 ml, the spore population was confirmed to be 10$^7$ spores/0.1 ml.

The temperature of the incubators was continually monitored to assure constant temperatures throughout the incubation period. The temperature range of the 37° C. incubator was 37.3° C. to 37.4° C. The temperature range of the 42° C. incubator was 41.6° C. to 42.1° C. The sterility lab was cleaned and particle counts were taken to assure that microbial contamination for the sterility test laboratory was within 10,000 particles per cubic foot at 0.5 microns and less than 70 particles per cubic foot at 5.0 microns, and within the laminar flow hood less than 100 particles per cubic foot at 0.5 microns.

Transfer to 50% EtOH

The 50% EtOH was filter sterilized through a 0.2 $\mu$filter unit. Each transfer was performed individually. First, approximately 80 ml of the 50% ethanol was poured into a white plastic sterile jar. The components were transferred from the iodine solutions to the 50% EtOH using sterile forceps. The transfer of jars inoculated with *B. subtilis* were made outside the sterility testing laboratory within the biological safety hood. During the transfer, observations of the tissue, solution condition, and color were made and recorded. Table 5 below outlines these observations. All jars sat at room temperature for approximately 24 hours before conducting the sterility test.

Controls: The filtered 50% EtOH was tested for sterility (as described below in Sterility Testing). Two TSA plates were left open in the hood during the transfer, and then incubated at 35° C. for 48 hours. During the transfers, microbial air sampling was performed within the sterility testing laboratory and in the microbiology laboratory.

Sterility Testing of Components

After approximately 24 hours in the 50% EtOH, the components of each jar #16–18 and #26–28 were tested for sterility. Individually, the contents from each jar were transferred to 200 ml of TSB. The broth was incubated for 7 days at 35°±2° C. Each day the media was examined for growth.

Sterility Testing of Iodine/Ethanol Solutions

Individually, each solution from each jar #16–18 and #26–28 was filtered through a 0.45 $\mu$filter on a 3-place filter holder manifold. Testing was conducted in the biological safety hood in the general microbiology laboratory area. Each filter was rinsed three (3) times with 100 ml of peptamin. The filter was placed into 200 ml of TSB and incubated at 35°±2° C. for 7 days. Each day the media was examined for growth.

Controls: During the sterility test in the biological safety cabinet, one jar of medium was left open continuously. Upon completion of the tests the jar was closed and incubated with the others. One forceps was dipped into 10 ml of TSB then incubated at 35° C. One filter was rinsed three (3) times with 100 ml of peptamin, placed into 200 mil of TSB, incubated and observed for growth.

Observations

Table 5 outlines the tissue condition, tissue color, and iodine solution color after incubation in iodine solutions:

TABLE 5

| Jar | Tissue Conditions | Tissue Color | Iodine Soln Color |
|---|---|---|---|
| 10 | fresh, pliable | 2 leaflets-white, 2 leaflets-629C* | (no I$_2$) |
| 11 | fresh, | tissue = 557C*, components = off | 580C* |

TABLE 5-continued

| Jar | Tissue Conditions | Tissue Color | Iodine Soln Color |
|---|---|---|---|
|  | pliable | white (yellowish) |  |
| 12 | fresh, pliable | tissue = 579C*, components = off white (yellowish) | " |
| 13 | fresh, pliable | tissue = 579C*, components = off white (yellowish) | " |
| 14 | fresh, pliable | tissue = 557C*, components = off white (yellowish) | " |
| 15 | fresh, pliable | tissue = 557C*, components = off white (yellowish) | " |
| 16 | fresh, pliable | tissue = 557C*, components = off white (yellowish) | " |
| 17 | fresh, pliable | tissue = 564C*, components = off white (yellowish) | 395C* |
| 18 | fresh, pliable | tissue = 564C*, components = off white (yellowish) | 387C* |
| 19 | fresh, pliable | tissue = 629C*, components = no discoloration | — (ethanol) |
| 20 | fresh, pliable | tissue = 630C*, components = no discoloration | 636C* (no iodine) |
| 21 | fresh, pliable | tissue = 630C*, components = no discoloration | 636C* (no iodine) |
| 22 | fresh, pliable | tissue = 630C*, components = no discoloration | 629C* |
| 23 | fresh, pliable | tissue = 629C*, components = no discoloration | 636C* |
| 24 | fresh, pliable | tissue = 629C*, components = no discoloration | 628C* |
| 25 | fresh, pliable | tissue = 629C*, components = no discoloration | " |
| 26 | fresh, pliable | tissue = 629C*, components = no discoloration | " |
| 27 | fresh, pliable | tissue = 629C*, components = no discoloration | 635* |
| 28 | fresh, pliable | tissue = 629C*, components = no discoloration | 628* |
| 29 | fresh, pliable | — | — |

*Color matches the numbering system of the Pantone Color Chart 1991.

From the foregoing results, it was concluded that tissue treated with iodine sterilization solutions may exhibit slight staining; however, any staining appeared to be temporary only, and, in fact, appeared to be reversed by subsequent soaking in 50% ethanol.

Results From Controls

Table 6 shows the result of the controls mentioned in the procedure. All of the controls were negative for growth and thus sterile.

TABLE 6

| Test Controls | Results |
|---|---|
| Open TSA Plates | Negative |
| Forcep | Negative |
| System Control | Negative |
| Ethanol | Negative |
| Negative Control |  |
| Air Sampling |  |
| Sterility Lab | No growth |
| General Lab | 4 CFU/ft$^3$, no B. subtilis |

Sterility Test Results

Condition 1

As seen in Table 7, the tissue valve components, the iodine solution, and the ethanol which was exposed to Condition 1 all were sterile for jars 16 to 18. The inoculated iodine without components (jar C1+) also was sterile.

TABLE 7

| Sample | Results |
|---|---|
| jar 16 components | Sterile* |
| jar 17 components | Sterile |
| jar 18 components | Sterile |

TABLE 7-continued

| Sample | Results |
|---|---|
| jar 16 iodine solution | Sterile |
| jar 17 iodine solution | Sterile |
| jar 18 iodine solution | Sterile |
| jar 16 EtOH | Sterile |
| jar 17 EtOH | Sterile |
| jar 18 EtOH | Sterile |
| jar C1− | Sterile |
| jar C1+ | Sterile |

*Sterile = No growth was detected

Condition 2

As seen in Table 8, the tissue valve components, the iodine solution, and the ethanol from Condition 2 all were non-sterile. Colony morphology and gram staining confirmed that all non-sterile jars contained B. subtilis. The inoculated iodine solution without components from Condition 2 (C2+) was sterile. All jars of media which were positive for growth were streaked onto a TSA plate and incubated at 35° C. All growth was confirmed to be B. subtilis by colony morphology and a gram stain.

TABLE 8

| Sample | Results |
|---|---|
| Jar 26 Components | Non-Sterile |
| Jar 27 Components | Non-Sterile |
| Jar 28 Components | Non-Sterile |
| Jar 26 Iodine Solution | Non-Sterile |
| Jar 27 Iodine Solution | Non-Sterile |
| Jar 28 Iodine Solution | Non-Sterile |
| Jar 26 EtOH | Non-Sterile |
| Jar 27 EtOH | Non-Sterile |
| Jar 28 EtOH | Non-Sterile |
| Jar C2− (un-inoculated) | Sterile |
| Jar C2+ (inoculated) | Sterile |

Experiment 10

The purpose of this experiment was to challenge a candidate sterilant solution (0.1% iodine solution buffered to pH 6.5) with Pseudomonas aeruginosa, Bacillus subtilis, and Staphylococcus aureus.

The samples were inoculated at approximately $1 \times 10^6$ per jar, $1 \times 10^7$ per jar for B. subtilis, with the following organisms:

B. subtilis, spore suspension, NAmSA;
P. aeruginosa, ATCC 9027;
S. aureus, ATCC 6538.

The candidate sterilant contained 0.1% iodine phosphate buffered to pH 6.5 (preparation already described), and the incubation lasted for 48±2 hours at 37°±2° C. The following test samples were used:

Samples innoculated with B. subtilis:
1 (a–c): no tissue valve components—3 jars;
1 (d–h): with tissue valve components—5 jars;
Samples innoculated with P. aeruginosa:
2 (a–c): no tissue valve components—3 jars;
2 (d–h): with tissue valve components—5 jars;
Samples innoculated with S. aureus:
3 (a–c): no tissue valve components—3 jars;
3 (d–h): with tissue valve components—5 jars;
Samples not innoculated:
CI: iodine only, no tissue valve components—4 jars;
CIC: with tissue valve components—1 jar;
CE: ethanol solution—4 jars.

Unless otherwise stated, all tissue was photooxidatively stabilized. The color and pH of the iodine solution from jar CIC was noted, and the appearance before and after transfer into 50% ethanol was noted.

The following results were obtained in the following samples, each of which contained tissue valve components in addition to the iodine and inoculum:

No growth in five samples with $10^6$ *Escherichia coli;*
No growth in five samples with $10^6$ *Staphylococcus aureus;*
Growth in 1 of 5 samples with $10^7$ *Bacillus subtilis.*

Control samples inoculated in the absence of tissue valve components all indicated no surviving microorganisms.

Although some growth was noted in the *B. subtilis* samples, this does not mean that the solution failed to achieve a required kill rate. *B. subtilis* is one of the most difficult microorganisms to kill, and the *B. subtilis* samples were inoculated with $10^7$ spores. It should not be necessary to kill $10^7$ *B. subtilis* spores in order to pass regulatory standards.

Experiment 11

Experiment 10 was repeated using *Escherichia coli, Candida albicans,* and *Bacillus subtilis.* The samples again contained tissue valve components in addition to the iodine solution and inoculum. Similar results were obtained and given a similar interpretation:

No growth in five samples with $10^6$ *E. coli;*
No growth in five samples with $10^6$ *C. albicans;*
Growth in 2 of 5 samples with $10^7$ *B. subtilis.*

Control samples (3 for each microorganism) inoculated in the absence of tissue valve components all indicated no surviving microorganisms.

Experiment 12

The following experiment was designed to examine the effect that refreshing the sterilization solution at intervals would have on microbial kill by various solutions. Samples were prepared to contain all tissue valve components, 80 mL iodine sterilants (at 0.01, 0.02, 0.05, or 0.10% iodine—six samples at each concentration), and $1.35 \times 10^6$ *Bacillus subtilis.* Controls contained no components. At 24 hr (one-half of the sterilization cycle), components (when present) were transferred to a fresh polypropylene jar with fresh iodine. To four samples (at each concentration) was added a filter obtained from the filtration of the iodine solution from that sample. This was done to carry over any surviving organisms.

The results are reflected in the following chart, in which the headings have the following meanings:

Sample—sample number
Iodine—concentration (each) of iodine, KI, and NaI
Components—presence or absence of tissue valve components
Filter added back—all iodine samples were filtered at 24 hours after component transfer to fresh iodine. In four samples at each iodine concentration (e.g., 1A-1D) the filters were tested for sterility. In the four other samples (e.g., 1A'-1D'), the filters were added to the new iodine.
Filter sterile? (24 hour)—The filters not added to the new iodine were tested for sterility. Y indicates no Growth.
Final solution sterile—After the total 48 hour sterilization cycle, solution was tested for sterility.

TABLE 9

| Sample | Iodine Conc. | Components | Filter Added Back | Filter Sterile? (24 hr.) | *Final Solution Sterile? |
|---|---|---|---|---|---|
| 1A/1A' | 0.01 | — | N/Y | Y | Y/Y |
| 1B | 0.01 | + | N | N | N |
| 1C | 0.01 | + | N | N | N |
| 1D | 0.01 | + | N | N | N |
| 1B' | 0.01 | + | Y | NA | N |
| 1C' | 0.01 | + | Y | NA | N |
| 1D' | 0.01 | + | Y | NA | Y |
| 2A/2A' | 0.02 | — | N/Y | Y | Y/Y |
| 2B | 0.02 | + | N | N | N |
| 2C | 0.02 | + | N | N | N |
| 2D | 0.02 | + | N | N | N |
| 2B' | 0.02 | + | Y | NA | N |
| 2C' | 0.02 | + | Y | NA | N |
| 2D' | 0.02 | + | Y | NA | N |
| 3A/3A' | 0.05 | — | N/Y | Y | Y/Y |
| 3B | 0.05 | + | N | Y | Y |
| 3C | 0.05 | + | N | N | Y |
| 3D | 0.05 | + | N | N | Y |
| 3B' | 0.05 | + | Y | NA | Y |
| 3C' | 0.05 | + | Y | NA | Y |
| 3D' | 0.05 | + | Y | NA | Y |
| 4A/4A' | 0.10 | — | N/Y | Y | Y/Y |
| 4B | 0.10 | + | N | Y | Y |
| 4C | 0.10 | + | N | Y | Y |
| 4D | 0.10 | + | N | Y | Y |
| 4B' | 0.10 | + | Y | NA | Y |
| 4C' | 0.10 | + | Y | NA | Y |
| 4D' | 0.10 | + | Y | NA | Y |

*Final solution tested for sterility for samples without/with filter added back (this applies only to the no component samples).

The foregoing results indicate that changing the iodine based solution during the cycle—here at mid-point—may increase the efficacy of the solution in killing microorganisms.

Experiment 13

The following experiment was conducted to determine whether or not a solution of pure elemental iodine would be capable of safely and effectively sterilizing the tissue implants.

Experimental conditions
80 mL 0.1% iodine (with and without each of KI and NaI)
pH 6.5, 1X PBS
2% total ethanol
$4 \times 1''$ squares bovine photofixed tissue
$1.35 \times 10^6$ *B. subtilis* spores
Incubation for 48 hours at 37° C.

After incubation, sterility tests were performed on tissue samples, iodine sterilant sample, and filter obtained by filtering the remainder of the sterilant. The following results were obtained.

TABLE 10

| | | Sterility results | | |
|---|---|---|---|---|
| Sterilant | Cotents | Tissue Sterile? | Solution Sterile? | Filter Sterile? |
| iodine only | tissue + spores | 3/3-Yes | 3/3-Yes | ⅓-Yes ⅔-No |
| iodine only | tissue only | NA | NA | NA |
| iodine only | spores only | 3/3-Yes | 3/3-Yes | 3/3-Yes |
| +iodides | tissue + spores | 3/3-Yes | 3/3-Yes | 3/3-Yes |
| " | tissue only | NA | NA | NA |
| " | spores only | 3/3-Yes | 3/3-Yes | 3/3-Yes |

TABLE 11

| Sample | Shrink temperature results | | |
|---|---|---|---|
| | A | B | C |
| Iodine with no iodides | 65 (0.2) | 64.6 (0.4) | 65.1 (0.1) |
| Iodine with NaI & KI | 63.9 (1.3) | 59.6 (2.4) | 59.7 (2.3) |

(Numbers in parentheses are degrees below control which is a photooxidized and nonsterilized bovine leaflet. Controls are included in each shrink temperature run.)

From these results, it was concluded that:
1) An iodine solution, without stabilizing salts, is capable sterilizing tissue implants; and
2) The efficacy of an elemental iodide solution without stabilizing salts is less than the efficacy of a solution with such salts. Therefore, it is possible that the stabilizing salts maintain the iodine in an active (antimicrobial) form.

IMPLANTATION STUDIES

Experiment 14

In order to assess the efficacy of the present sterilization method in vivo, tissue valves that had been fixed and sterilized using glutaraldehyde were compared to tissue valves that had been fixed and sterilized according to the methods described herein. The implanted valves included clinically available Carpentier-Edwards porcine valves and Carbomedics valves. The valves were implanted in sheep for a period varying between 26–157 days. The valves later were explanted and studied for evidence of calcification and other damage.

Several of the animals in the study suffered early deaths which appeared to be due to infection and related thrombosis. A 10–20% infection rate is expected in animal related implant studies. One control valve failed early due to a leaflet tear, and another control valve failed early because of a size mismatch resulting in stent distortion. Two of the valves were treated with a higher temperature and lower pH than preferred, which is known to cause collagen denaturation, but at a relatively low pH. These two valves did not show any calcification, and performed satisfactorily with no degenerative problems.

Figure 6A:
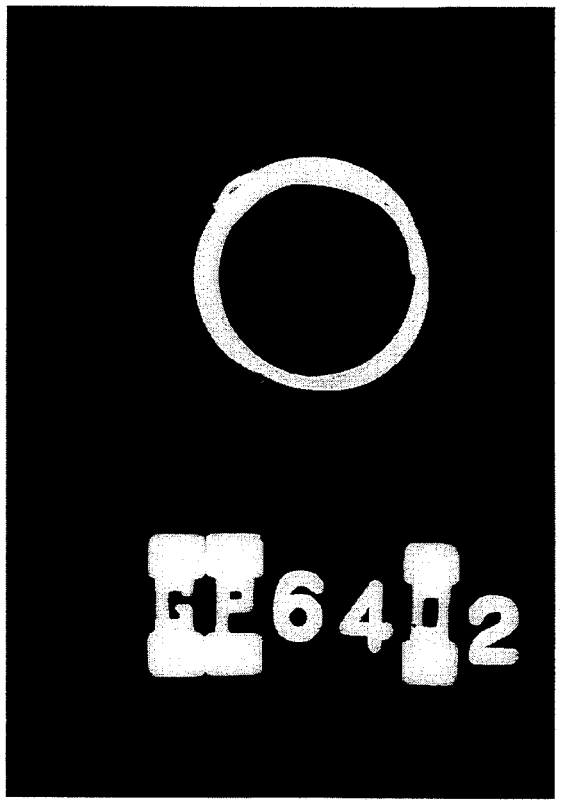
FIGS. 6A and 6B are photographs of x-rays of explanted tissue valves which were treated according to the present invention which shows no evidence of calcification.
Figure 6B:
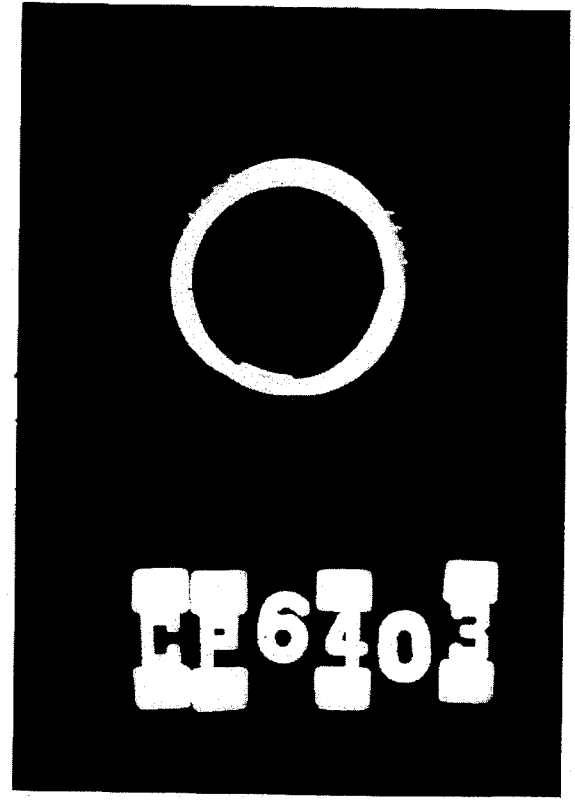
Figure 7A:
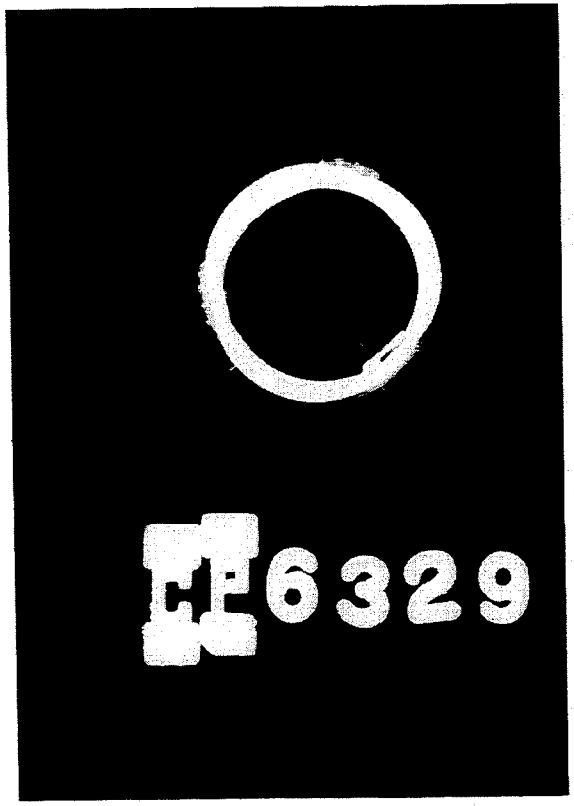
FIGS. 7A, 7B, and 7C are photographs of x-rays of explanted tissue valves which were treated with glutaraldehyde, and which show evidence of calcification.
Figure 7B:
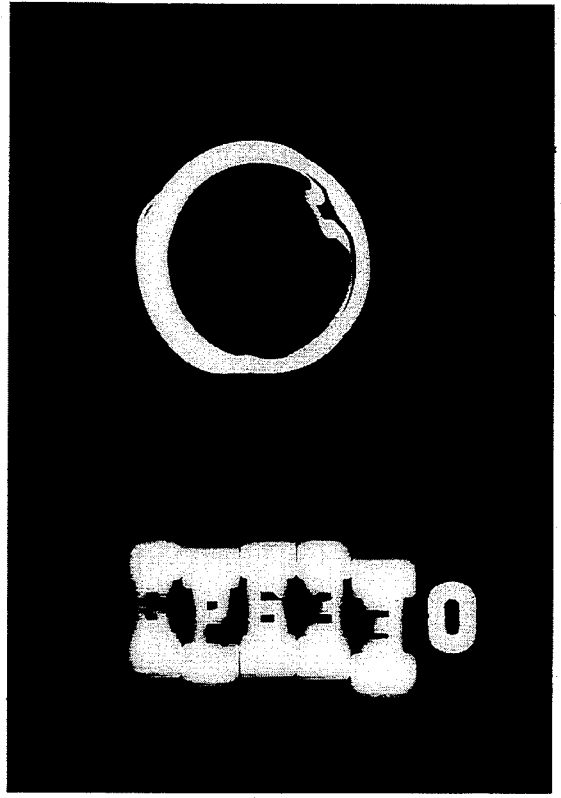
Figure 8A:
FIGS. 8A and 8B are photographs of x-rays of explanted Carpentier-Edwards Porcine tissue valves which were treated with glutaraldehyde, and which show evidence of calcification.
Figure 7C:
Figure 8B:

All of the glutaraldehyde treated valves exhibited some degree of calcification with short implant durations. The calcification can be seen at the coaption points in FIGS. 7A, 7B, and 7C and in FIGS. 8A and 8B, which are photographs of x-rays of representative explanted tissue valves treated with glutaraldehyde. All but one of the valves treated according to the methods described herein performed successfully through a five month implant time, did not show any calcification, and performed with no degenerative problems. The other valve failed due to a non-valve related problem after two months, and also did not show any calcification. The absence of calcification can be seen in FIGS. 6A and 6B, which are photographs of x-rays of explanted tissue valve treated according to the present invention.

Experiment 15

Six valves (designated as "Zeta__") treated as described herein were implanted and explanted after the following time periods with the following results:

The following samples gave a physiologic gradient and no regurgitation via angiography. The tissue was in good shape with good leaflet flexibility and no visual calcification. Zeta 25, explanted after 163 days; Zeta 26, explanted after 161 days; Zeta 27, explanted after 160 days; and Zeta 30, explanted after 154 days.

Zeta 28, explanted after 159 days, demonstrated a higher than expected gradient and had significant regurgitation; however, upon valve retrieval, it was observed that sutures were looped over two stent posts which interfered with the functionality of the leaflets. The animal was in good health and the valve functioned adequately enough, even with the suture loops to keep the animal alive. The extra stress of the loops would be expected to result in rapid calcification and early animal death in a glutaraldehyde treated valve.

Zeta 29, explanted after 155 days, had a good gradient but demonstrated slight regurge, as indicated by a wisp of dye backflowing after valve closure. The explant revealed one lazy leaflet which might have resulted in slight prolapse. This possibly is due to slightly different tissue stretch, leaflet-to-leaflet. Again, as in other explants, the valve was clean and the leaflets looked good.

One of skill in the art will appreciate that many modifications may be made to the embodiments described herein and explained in the accompanying figures without departing from the spirit of the present invention. Accordingly, the embodiments described herein are illustrative only and are not intended to limit the scope of the present invention.

We claim:

1. A method for sterilizing a medical device intended for implantation inside the body of a mammal comprising the steps of:
   providing an implant comprised at least in part of excised proteinaceous tissue; and
   incubating said implant in a germicidal solution comprising elemental iodine at a concentration, a temperature, and for a time effective to sterilize said implant without damaging said implant, said germicidal solution having a pH between about 5.0–6.8.

2. The method of claim 1 wherein said germicidal solution further comprises iodine stabilizing salts.

3. The method of claim 2 wherein said iodine stabilizing salts are potassium iodide and sodium iodide.

4. The method of claim 1 wherein said elemental iodine comprises about 0.01% to 0.20% by weight of said solution.

5. The method of claim 2 wherein said elemental iodine comprises about 0.01% to 0.20% by weight of said solution.

6. The method of claim 3 wherein said elemental iodine comprises about 0.01% to 0.20% by weight of said solution.

7. The method of claim 3 wherein said potassium iodide and sodium iodide each comprise about 0.01% to 0.40% by weight of said solution.

8. The method of claim 7 wherein said elemental iodine, potassium iodide, and sodium iodide each comprise about 0.09% to 0.11% by weight of said solution.

9. The method of claim 8 wherein said pH is between about 6.4 to 6.6.

10. The method of claim 1 wherein said time of exposure is between about three hours and two weeks and said incubation temperature is between about 20° C. and 50° C.

11. The method of claim 9 wherein said time of exposure is about two days and said incubation temperature is between about 35° C. and 39° C.

12. The method of claim 9 where said time of exposure comprises two twenty-four hour stages wherein said iodine solution is refreshed after a first twenty four hour stage.

* * * * *